(12) United States Patent
Michnick et al.

(10) Patent No.: US 7,855,167 B2
(45) Date of Patent: *Dec. 21, 2010

(54) IN VIVO SCREENING OF PROTEIN-PROTEIN INTERACTIONS WITH PROTEIN-FRAGMENT COMPLEMENTATION ASSAYS

(75) Inventors: Stephen William Watson Michnick, Westmount (CA); Ingrid Remy, Montreal (CA); Jane Lamerdin, Livermore, CA (US)

(73) Assignee: ODYSSEY THERA, Inc., San Ramon, CA (US)

( * ) Notice: Subject to any disclaimer, the term of this patent is extended or adjusted under 35 U.S.C. 154(b) by 770 days.

This patent is subject to a terminal disclaimer.

(21) Appl. No.: 10/728,355

(22) Filed: Dec. 5, 2003

(65) Prior Publication Data

US 2004/0229240 A1    Nov. 18, 2004

Related U.S. Application Data

(63) Continuation-in-part of application No. 09/603,885, filed on Jun. 26, 2000, now Pat. No. 6,897,017, which is a continuation-in-part of application No. 09/017,412, filed on Feb. 2, 1998, now Pat. No. 6,270,964.

(60) Provisional application No. 60/141,210, filed on Jun. 26, 1999.

(51) Int. Cl.
| | |
|---|---|
| *C40B 20/08* | (2006.01) |
| *C40B 30/10* | (2006.01) |
| *C12Q 1/70* | (2006.01) |
| *C12P 21/04* | (2006.01) |
| *C07H 21/02* | (2006.01) |
| *C07H 21/04* | (2006.01) |

(52) U.S. Cl. .................... 506/6; 506/12; 435/5; 435/6; 435/69.7; 536/23.1; 536/23.5

(58) Field of Classification Search .................... 506/6, 506/12; 435/5, 6, 69.7; 536/23.1, 23.5
See application file for complete search history.

(56) References Cited

U.S. PATENT DOCUMENTS

| | | | |
|---|---|---|---|
| 6,270,964 B1 * | 8/2001 | Michnick et al. ............... 435/6 |
| 6,780,599 B2 * | 8/2004 | Hamilton et al. ............. 435/7.1 |
| 6,897,017 B1 * | 5/2005 | Michnick et al. ............... 435/6 |
| 2002/0146701 A1 * | 10/2002 | Hamilton et al. ............... 435/6 |
| 2003/0003506 A1 * | 1/2003 | Umezawa et al. ............ 435/7.1 |

FOREIGN PATENT DOCUMENTS

WO    WO 0208766    *   1/2002

OTHER PUBLICATIONS

Ormo et al. Science. vol. 273: 1392-1395; 1996.*

* cited by examiner

*Primary Examiner*—Sue Liu
(74) *Attorney, Agent, or Firm*—Isaac A. Angres

(57) ABSTRACT

The present invention describes rapid methods to screen for biomolecular interactions in vivo based on protein fragment complementation assays (PCA). We have demonstrated an in vivo library-versus-library screening strategy that has numerous applications in the identification of novel protein-protein interactions and in directed evolution. Also we demonstrate the detection of protein-protein interactions starting with defined (full-length) cDNAs, and the concomitant generation of functional assays that provide initial validation of the cDNA products as being biologically relevant. Also, we screened a large cDNA collection using automated PCA, combined with quantitative detection of protein-protein complexes. The invention enables bait-vs.-library, library-vs.-library and defined gene screening in any type of cell or cellular context, and using a wide range of reporters and detection methods. The invention allows for identifying and validating genes involved in any cellular process and also provide assays to study effects of potential drugs, or gene knockouts on specific pathways.

19 Claims, 17 Drawing Sheets

Figure 1
(A) Library constructs
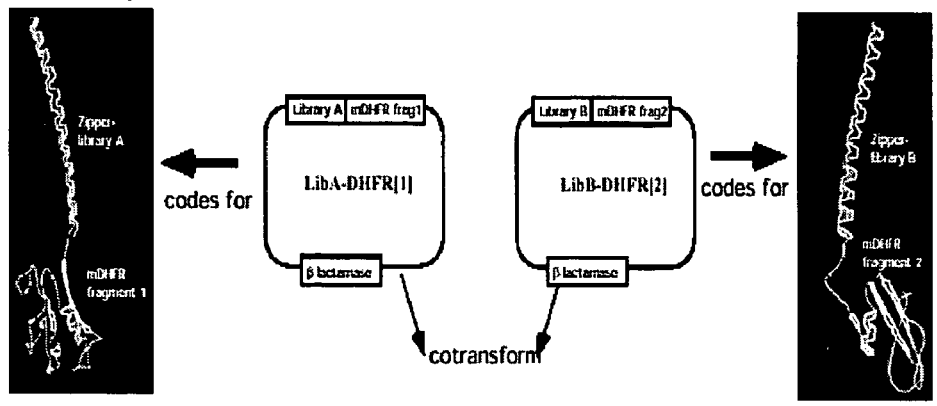
(B) Single-step selection
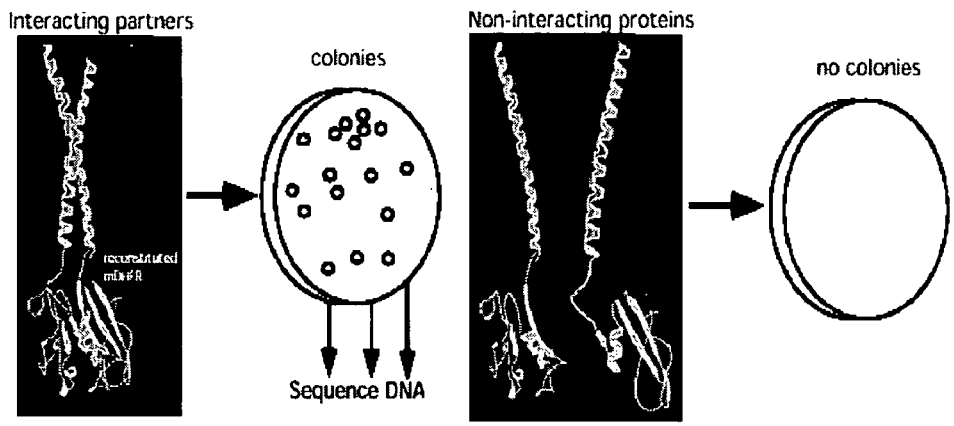
(C) Competition selection
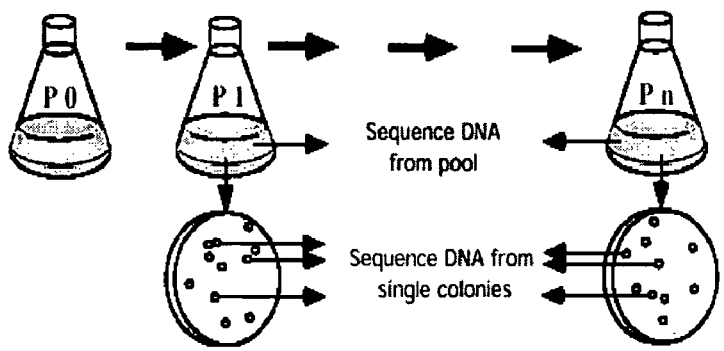

Fig. 6A 148 combinations tested • 65 potential interactions • 14 observed and 5 novel

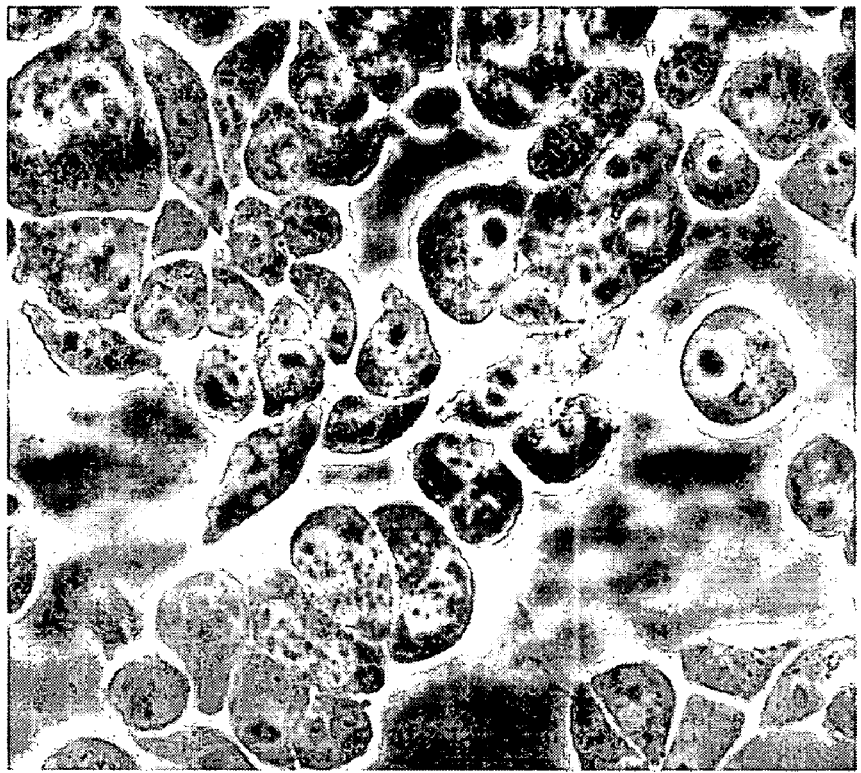

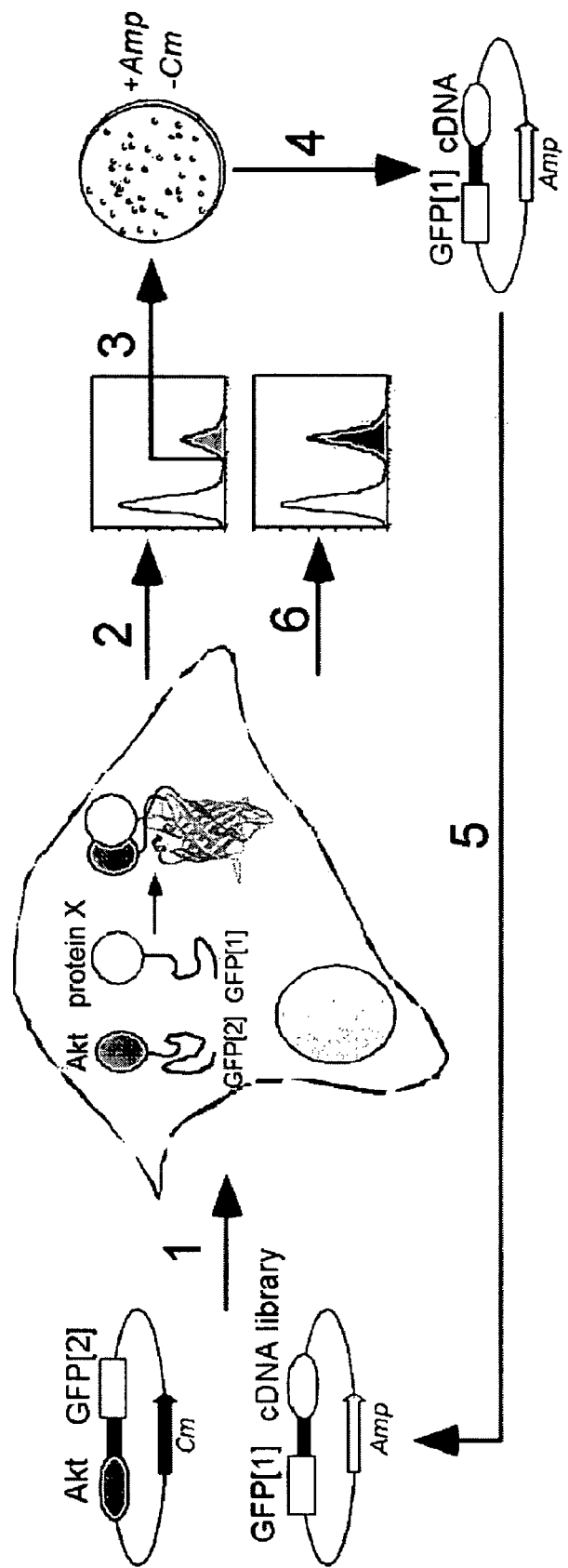

Fig. 10
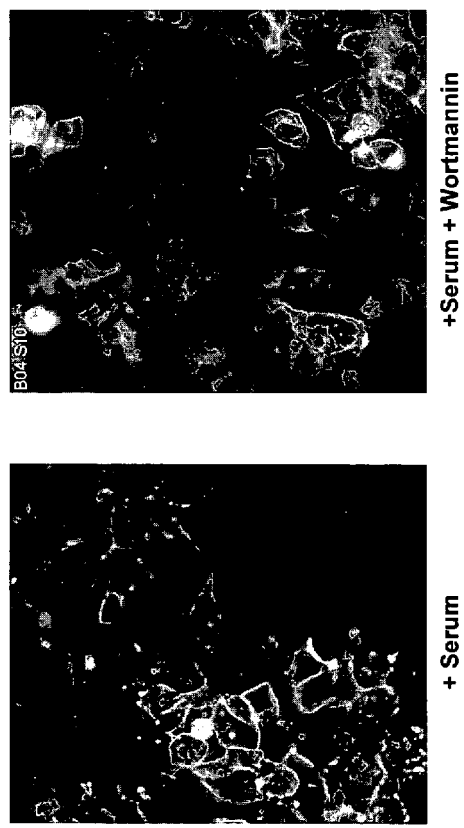
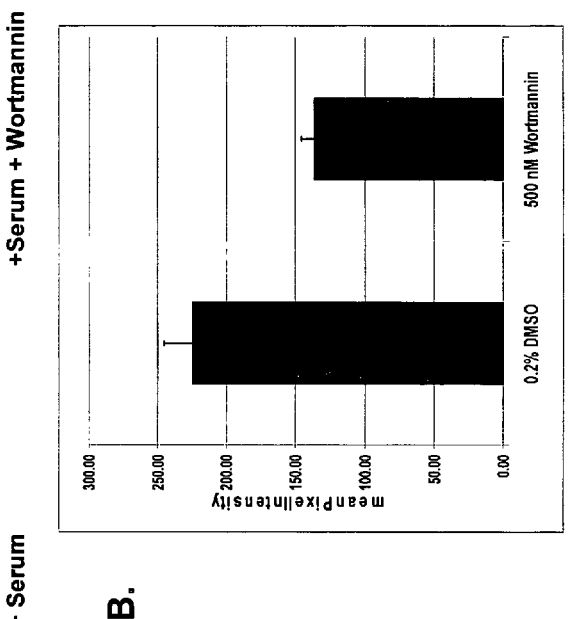

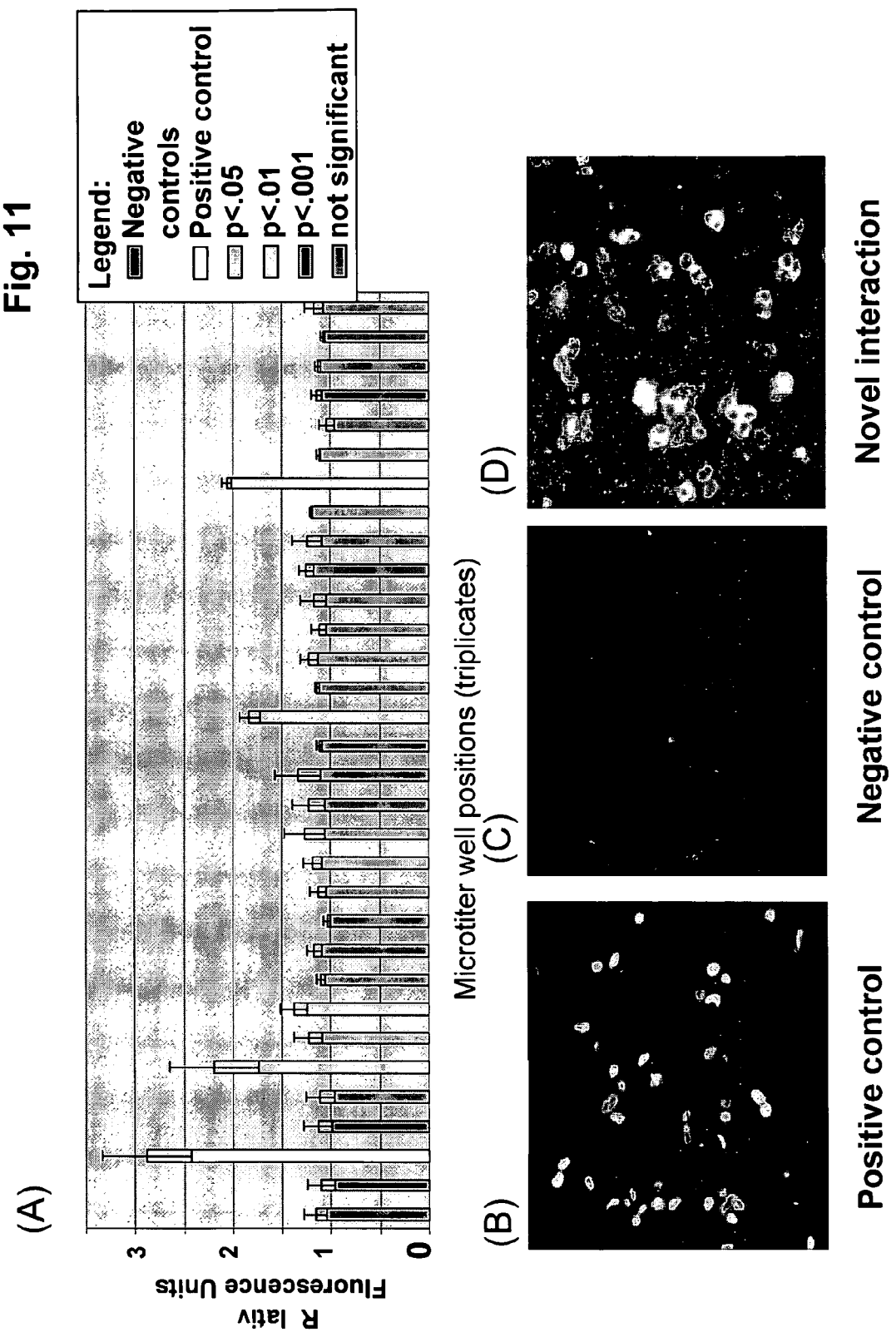

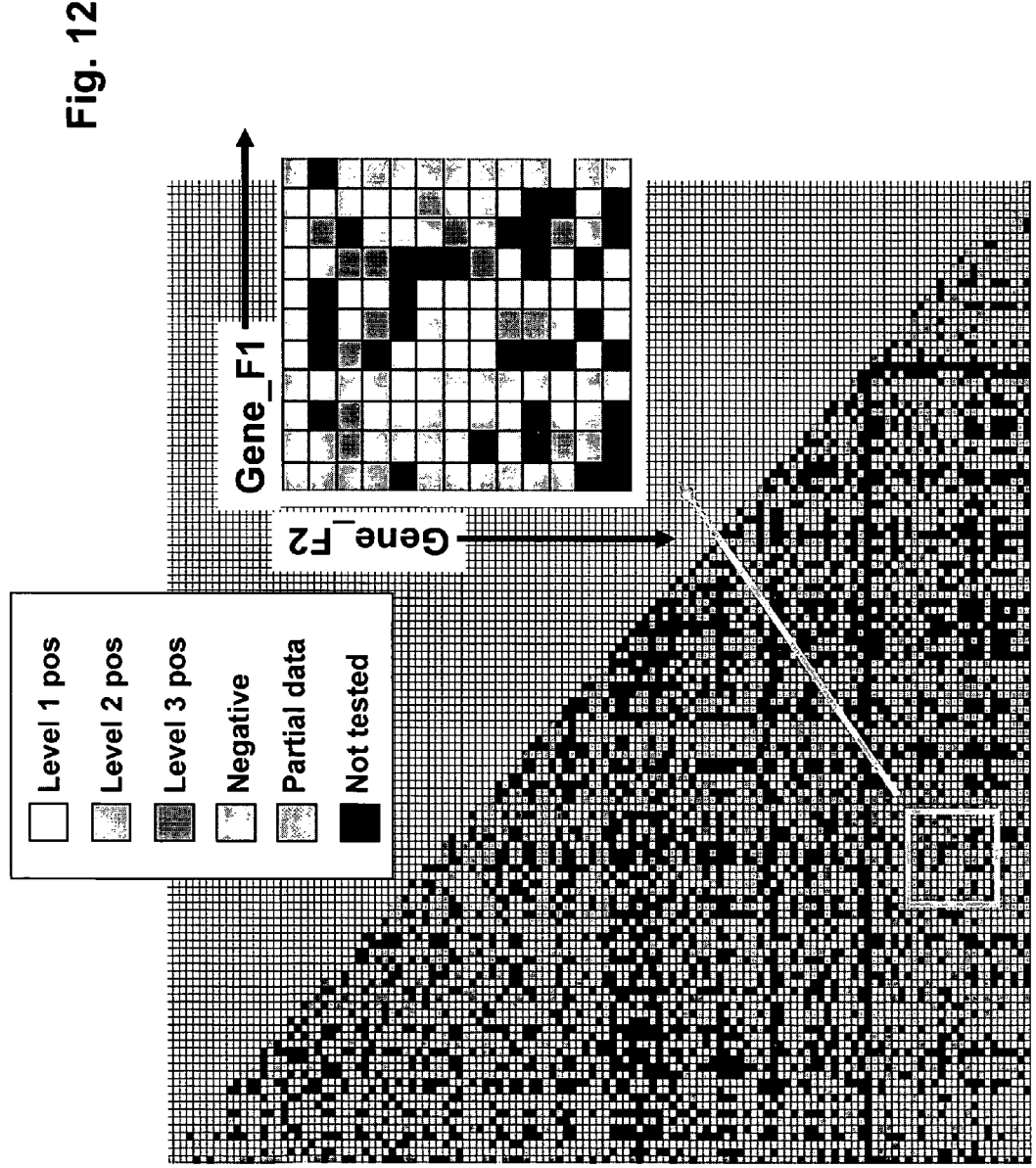

Fig. 13

| | Working Definition | All Orientations | Unique |
|---|---|---|---|
| Assays in triplicate | | 9931 (29,793 single) | 5773 (17,139 single) |
| Pos, Level 1 | Plate reader pval$_{mean}$ <= 0.001<br>Image analysis score > 16<br>Fold increase >= 1.3 | 227 (2.3%) | 205 (3.6%) |
| Pos, Level 2 | Plate reader pval$_{mean}$ <= 0.01<br>Image analysis score > 8<br>Fold increase >= 1.2 | 1014 (10.2%) | 730 (12.6%) |
| Pos, Level 3 | Plate reader pval$_{mean}$ < 0.05<br>Image analysis score >= 2<br>Fold increase > 1 | 994 (10.0%) | 640 (11.1%) |
| Negative | Plate reader pval$_{mean}$ < 0<br>or >= 0.05<br>Image analysis score < 2 | 6143 (61.9%) | 3542 (61.4%) |
| Partial data | Plate reader or image data only | 20 (0.2%) | 19 (0.3%) |
| Discordant | Image and Plate reader scores discordant | 1533 (15.4%) | 637 (12.0%) |

Fig. 14

| Assays in triplicate | Positive Control | Negative Control | Single DNA | No DNA |
|---|---|---|---|---|
| | 459 | 459 | 459 | 459 |
| Pos, Level 1 | 159 (34.7%) | 0 (0%) | 0 (0%) | 0 (0%) |
| Pos, Level 2 | 264 (57.5%) | 0 (0%) | 0 (0%) | 0 (0%) |
| Pos, Level 3 | 13 (2.8%) | 0 (0%) | 1 (0.2%) | 0 (0%) |
| Negative | 6 (1.3%) | 451 (98.3%) | 423 (92.2%) | 426 (92.8%) |
| Partial data | 15 (3.3%) | 8 (1.7%) | 8 (1.7%) | 8 (1.7%) |
| Discordant | 2 (0.4%) | 0 (0%) | 27 (5.9%) | 25 (5.5%) |

Excluding Partial and Discordant Data:

True positives = 98.6%
True negatives = 99.9%
False positives = 0.08%
False negatives = 1.4%

SEQUENCE LISTING

```
<160> NUMBER OF SEQ ID NOS: 5

<210> SEQ ID NO 1
<211> LENGTH: 32
<212> TYPE: PRT
<213> ORGANISM: Artificial Sequence
<220> FEATURE:
<223> OTHER INFORMATION: leucine zipper-forming peptide designed from
      hybrid libraries between GCN4 and c-Jun/c-Fos

<400> SEQUENCE: 1

Val Ala Gln Leu Glu Glu Lys Val Lys Thr Leu Arg Ala Gln Asn Tyr
1               5                   10                  15

Glu Leu Lys Ser Arg Val Gln Arg Leu Arg Glu Gln Val Ala Gln Leu
            20                  25                  30

<210> SEQ ID NO 2
<211> LENGTH: 32
<212> TYPE: PRT
<213> ORGANISM: Artificial Sequence
<220> FEATURE:
<223> OTHER INFORMATION: leucine zipper-forming peptide designed from
      hybrid libraries between GCN4 and c-Jun/c-Fos

<400> SEQUENCE: 2

Val Asp Glu Leu Gln Ala Glu Val Asp Gln Leu Gln Asp Glu Asn Tyr
1               5                   10                  15

Ala Leu Lys Thr Lys Val Ala Gln Leu Arg Lys Lys Val Glu Lys Leu
            20                  25                  30
```

-continued

```
<210> SEQ ID NO 3
<211> LENGTH: 32
<212> TYPE: PRT
<213> ORGANISM: Artificial Sequence
<220> FEATURE:
<223> OTHER INFORMATION: leucine zipper-forming peptide designed from
      hybrid libraries between GCN4 and c-Jun/c-Fos

<400> SEQUENCE: 3

Val Ala Gln Leu Arg Glu Arg Val Lys Thr Leu Arg Ala Gln Asn Tyr
1               5                   10                  15

Glu Leu Glu Ser Glu Val Gln Arg Leu Arg Glu Gln Val Ala Gln Leu
            20                  25                  30

<210> SEQ ID NO 4
<211> LENGTH: 32
<212> TYPE: PRT
<213> ORGANISM: Artificial Sequence
<220> FEATURE:
<223> OTHER INFORMATION: leucine zipper-forming peptide designed from
      hybrid libraries between GCN4 and c-Jun/c-Fos

<400> SEQUENCE: 4

Val Asp Glu Leu Lys Ala Glu Val Asp Gln Leu Gln Asp Gln Asn Tyr
1               5                   10                  15

Ala Leu Arg Thr Lys Val Ala Gln Leu Arg Lys Glu Val Glu Lys Leu
            20                  25                  30

<210> SEQ ID NO 5
<211> LENGTH: 10
<212> TYPE: PRT
<213> ORGANISM: Artificial Sequence
<220> FEATURE:
<223> OTHER INFORMATION: flexible linker

<400> SEQUENCE: 5

Gly Gly Gly Gly Ser Gly Gly Gly Gly Ser
1               5                   10
```

IN VIVO SCREENING OF PROTEIN-PROTEIN INTERACTIONS WITH PROTEIN-FRAGMENT COMPLEMENTATION ASSAYS

This application is a continuation-in-part of U.S. Ser. No. 09/603,885, filed Jun. 26, 2000, now U.S. Pat. No. 6897017; which application is a continuation-in part of U.S. application Ser. No. 09/017,412 filed Feb. 2, 1998, now U.S. Pat. No. 6,270,964 granted Aug. 7, 2001; the entire contents of which are incorporated by reference herein, and this application also claims the priority benefit of U.S. provisional application No. 60/141,210 filed Jun. 26, 1999.

The following abbreviations are used throughout the present specification: PCA, protein-fragment complementation assays; mDHFR, murine dihydrofolate reductase; fMTX, fluorescein methotrexate; GFP, green fluorescent protein; YFP, yellow fluorescent protein; PKB, protein kinase B (also referred to as Akt); cDNA, complementary DNA; Win-Zip: dominant zipper pairs obtained from competition selection; WinZip-A1B1: original pair selected, comprising peptide A1 from libraryA and peptide B1 from libraryB; WinZip-A1B2 and WinZip-A2B1: optimized pairs comprising the original partner A1 or B1 and the new partner B2 or A2, respectively.

FIELD OF THE INVENTION

This invention relates generally to the fields of molecular biology, cell biology, and biochemistry. Specifically, this invention provides Protein-fragment Complementation Assay (PCA) methods and compositions for in vivo screening for protein-protein interactions. Examples are provided for screening any synthetic or natural library or gene collection of interest, including peptide libraries, cDNA libraries, and defined gene libraries. Methods are described for selecting a suitable reporter, conducting the screening, and biologically validating the resulting 'hits', using PCA. Screening for protein-protein interactions in vivo can be accomplished by survival-selection or by an optical readout such as fluorescence or appearance of color in a wide range of cell types ranging from bacterial to mouse and human cells. Screening for protein-protein interactions with PCA is shown to be straightforward, and provides for a broad, flexible and biologically relevant platform for discovery research.

BACKGROUND OF THE INVENTION

Many of the problems currently being studied in molecular biology and biochemistry share a common factor: they are governed by essential molecular interactions, which are often protein-protein interactions. Important examples are the identification and functional characterization of novel gene products, the dissection of proteins into structural or functional motifs and the testing of hypotheses about the physical basis of protein-protein interactions, whether in naturally-occurring proteins or in designed products. The highly successful yeast two-hybrid assay has been demonstrated to be very effective in genome-wide screening for interacting proteins (1,2). However, the yeast two-hybrid system has limitations when applied to the mapping of protein-protein interactions in higher eukaryotes. It would be an advantage either to screen or, at a minimum, to perform followup studies of interacting partners directly in the context of the cell in which the proteins function and in the correct subcellular compartment. For example, in the case of mammalian proteins, a mammalian cell instead of a yeast cell would be the preferred context for screening and biologically validating protein-protein interactions.

In addition, it would be an advantage to be able to construct screens based on a variety of library types and sources, including natural diverse libraries such as cDNA libraries or single-chain antibody libraries; synthetic diverse libraries such as peptide libraries; or defined libraries such as full-length gene collections. These needs could potentially be met by a protein-protein interaction technology that could be performed in vivo, in any cellular context, and with the ability to engineer the assay properties and assay stringency.

Also, as the study of interacting partners is a "two-dimensional" problem influenced by variations in either partner, it would be advantageous in certain cases to pan a library of proteins not against a single bait protein, but against a second library of proteins. To date, no large-scale library-vs-library selection of protein-protein interactions has been reported, because the available strategies are not amenable to this in any practical way.

Finally, it would be an advantage to have a screening technology that is suitable for scale-up and automation with a choice of instrumentation platforms.

PCA involves tagging proteins with polypeptide fragments derived by rationally dissecting a reporter. If two proteins that are tagged with complementary fragments interact, the fragments are brought into close proximity. The complementary fragments can then fold into an active conformation and re-constitute the activity of the reporter from which the fragments were derived. At its basic level, PCA is a general and flexible strategy that allows detection of protein-protein interactions in vivo and also allows measurement of the association and dissociation of protein-protein complexes in real time. PCA has unique features that make it a useful tool for molecular and cell biology:

- Molecular interactions are detected directly, not through secondary events such as transcription activation.
- A variety of detection methods can be used, including cell growth (e.g. survival-selection), fluorescent, colorimetric, luminescent and phosphorescent detection, depending on the choice of reporter.
- Proteins can be expressed in the relevant cellular context, reflecting the native state of the protein with the correct post-translational modifications other cellular proteins that are necessary, directly or indirectly, for controlling the interactions that are being measured by the PCA.
- Because protein-protein complexes can be quantitated with PCA in the live cell context, immediate functional validation of protein-protein interactions can be achieved following library screening.

The present invention describes the uses of PCA in screening for protein-protein interactions in vivo and in validating the protein-protein interactions identified in the screens. Strategies, examples, and suitable reporters are provided for a range of cell types including bacterial, mammalian and human cells. Examples are provided for peptide libraries, cDNA libraries, and defined (full-length) gene libraries. The ability to choose among many different reporters allows a choice of readouts for the detection of a protein-protein interaction, including survival-selection, fluorescence, luminescence or phosphorescence or color. Examples are provided for survival-selection and fluorescence assays. The methods can be applied to library-vs.-library screening, bait-vs.-library screening, and interaction mapping of a full-length gene library. Moreover, these methods are amenable to scale-up and automation with a choice of instrumentation platforms for low-cost, large-scale screening.

DESCRIPTION OF THE DRAWINGS

FIG. 1: Library-vs.-library screening with PCA. (A) DNA constructs code for fusions between library proteins (shown as alpha-helical leucine zippers) and either fragment of murine DHFR (mDHFR). Fusions were created using either the wild-type or the mutant mDHFR fragment 2 (Ile114Ala), yielding LibA-DHFR[1] and LibB-DHFR[2] or LibB-DHFR [2:I114A], respectively. (B) Principle of the mDHFR-fragment complementation assay: *E. coli* cells are cotransformed with both fusion libraries in minimal medium, in the presence of IPTG (for induction of expression) and trimethoprim (for inhibition of the bacterial DHFR). If the library proteins heterodimerize, mDHFR can fold from the individual fragments resulting in active enzyme and bacterial growth. Both mDHFR fragments must be present, and dimerization of the fused proteins is essential, in order for cell propagation to be possible. The surviving clones are the result of "single-step selection" and can be directly analyzed by DNA sequencing. (C) "Competition selection" is undertaken by pooling clones from (B) in selective, liquid culture (passage 0 or P0), propagating the cells and diluting into fresh selective medium for further passages. An aliquot can be plated and the resulting colonies analyzed by DNA sequencing.

FIG. 6A. Mapping protein-protein interactions with DHFR PCA in mammalian cells. Full-length cDNAs corresponding to the indicated mammalian genes were fused to complementary DHFR fragments and tested for protein-protein interactions in CHO DUKX-B11 (DHFR-) cells. The grid represents all positive (green, +) and negative (red, −) interactions observed by survival selection. The x axis represents the fusions to the DHFR[1,2] fragment, and the y axis represents the fusions to the complementary DFHR[3] fragment. The orientations of the fusions (N-terminal or C-terminal) also are indicated. Cells were observed for the appearance of colonies for 5-21 days after incubation in selective medium. Only cells expressing fused interacting partners gave rise to colonies.

FIG. 6C. Generation of a red fluorescence assay with DHFR PCA. Reconstituted DHFR was detected with Texas Red-methotrexate. The dimerization of GCN4 leucine zipper (GCN4/GCN4) sequences was visualized by microscopy in transiently-transfected CHO DUKX-B11 cells. Left panel, leucine zipper complexes can be seen predominantly in the nucleus at 40× magnification; right panel, phase contrast image of the same cells.

FIG. 7. cDNA Library screening with PCA in mammalian cells. A human brain cDNA library was fused to fragment 1 of GFP (GFP[1]-cDNA library) and full-length Akt1 cDNA was fused to fragment 2 of GFP (Akt1-GFP[2]), in mammalian expression vectors harboring *E. coli* selection markers Ampicillin (Amp) and Chloramphenicol (Cm), respectively. In the first step (1) COS-1 cells were cotransfected with Akt1 (bait) and cDNA library (prey) fusions and a physical interaction between the bait and a prey protein induced the folding and reconstitution of GFP from its fragments, generating fluorescence. Positive clones were collected by fluorescence-activated cell sorting (FACS) (step 2), DNA extracted from the pools and transformed into *E. coli* grown on Amp plates to select only for plasmids harboring cDNA (step 3). Clones were picked, plasmids extracted and interaction of individual proteins with Akt1 were reconfirmed by cotransfecting COS-1 cells with the Akt1 fusion and individual cDNA fusions (step 5) and detection by FACS (step 6).

FIG. 10. Characterization of the Akt/PDK1 interaction in human cells with YFP PCA. The mutations S65G, S72A and T203Y were introduced into GFP[1] and GFP[2] (described above) by PCR, resulting in a YFP PCA. A stable cell line was generated by Zeocin selection of HEK293T cells co-expressing Akt-YFP[1] and YFP[2]-PDK1. The relative amount of reconstituted YFP, a measure of the interaction between the fused protein partners, was detected by fluorometric analysis in intact cells and was visualized by microscopy (20× magnification) in the absence or presence of serum +/− wortmannin. Cell nuclei were stained with DRAK5 (red). The histogram shows the effect of wortmannin on the fluorescence intensity (mean pixel intensity).

FIG. 11. Screening of protein-protein interactions in human cells with PCA. A semi-automated protocol was established for large-scale screening of protein-protein interactions in human cells with fluorescence detection in 96-well plates. The top panel displays a plot of the mean fluorescence intensity data for a typical YFP PCA assay plate. Each bar represents the mean of triplicate measurements from one of 32 possible interactions: 1 positive control (highlighted in yellow), 3 negative controls (highlighted in red), and 28 distinct gene pairs. Those gene pairs whose mean fluorescence intensity differed from that of the negative control at a statistically significant level are indicated. Error bars represent 95% confidence interval limits. The bottom panel contains representative images acquired by automated microscopy (Discovery-1 system) showing a positive control, a negative control, and a novel positive PCA with a predominantly cytoplasmic localization pattern. Blue objects represent nuclei stained with Hoescht 33342.

FIG. 12. Graphical depiction of the results of a large-scale screen of human protein-protein interactions. The y-axis represents fusions to YFP[2] (Gene-F2) and the x-axis represents fusions to YFP[1] (Gene-F1). The screening results were color-coded as follows: green, positive interaction; red, negative interaction; gray, indeterminate; black, not tested.

FIG. 13. Statistics for screening a full-length cDNA collection with YFP PCA.

FIG. 14. Control data statistics for semi-automated screening. Statistical cutoffs were as for FIG. 13.

SUMMARY OF THE INVENTION

Figure 2:
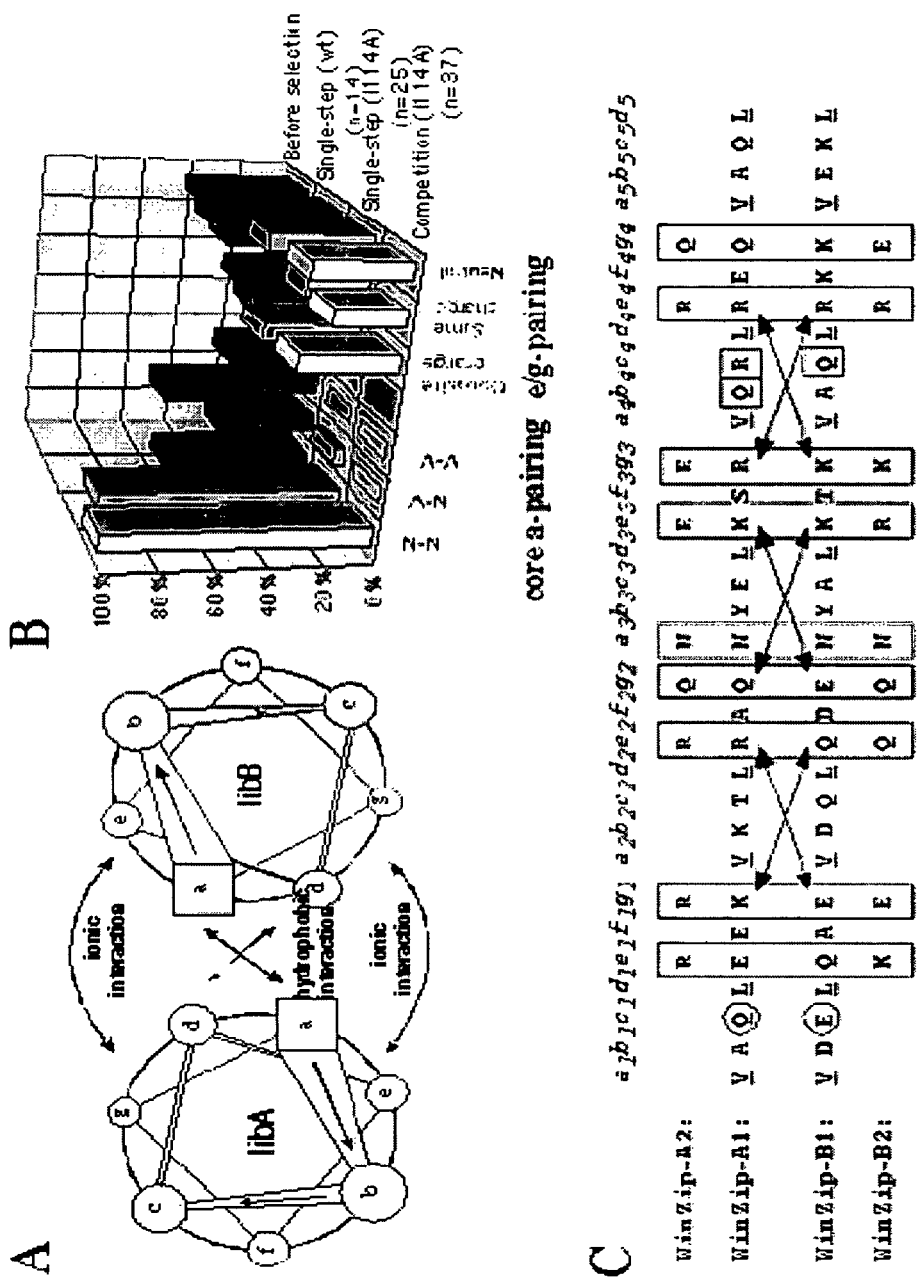
FIG. 2: (A) Schematic representation of a leucine zipper pair visualized from the N-terminus illustrating e/g-interactions and the hydrophobic core formed by the a- and d-positions. (B) Distribution of residues at the semi-randomized positions throughout selection. The number of zipper pairs sequenced is given in parentheses, save "Before selection" where the theoretical distribution is reported. Each pair carries one core a-pair and 6 e/g-pairs. Neutral e/g-pairs have one or both residues as Gln. In "Competition (I114A)" only clones from P6 to P12 (not from earlier passages) were considered for analysis. Thus, 37 individual clones were identified, giving rise to 10 unique sequences due to multiple occurrence of the enriched clones. The distributions were calculated according to the frequency of sequence occurrence (n=37). (C) Leucine zipper sequences WinZip-A1 (SEQ ID NO:1), WinZip-B1 (SEQ ID NO:2), WinZip-A2 (SEQ ID NO:3) and WinZip-B2 (SEQ ID NO:4) obtained after competition selection and chain shuffling. The heptad positions (a to g) are followed by the heptad number (1 to 5). Invariant residues from GCN4 are underlined. Clear boxes indicate the semi-randomized e- and g-positions (black outline) and core a-position (a3) (grey outline). Circled residues were designed to contribute to helix capping. Shaded residues were designed for the introduction of restriction sites. Other residues are from c-Jun (LibA) or c-Fos (LibB). Arrows indicate putative e/g-interactions.

The present invention is directed to a method for identifying an interacting set of molecules comprising: (A) generating fragments of a reporter molecule which have a directly or indirectly detectable activity when associated; (B) coupling first fragments to members of a first panel of molecules; (C) coupling second fragments to members of a second panel of molecules; (D) mixing the products of B) and C); (E) directly or indirectly testing for said activity; and (F) identifying the panel members whose interaction resulted in said activity and which thus form an interacting set.

The invention is also directed to a method for identifying an interacting set of molecules comprising: (A) identifying a first and a second panel of molecules whose mutual interaction is desired to be tested; (B) coupling molecules of said first panel to first fragments of a reporter molecule; (C) coupling molecules of said second panel to second fragments of said reporter molecule; (D) mixing the products of B) and C); (E) directly or indirectly testing for said activity; and (F) identifying the panel members whose interaction resulted in said activity and which thus form an interacting set.

The invention is further directed to a method of screening multiple panels of molecules against each other to determine the ability of individual panel members to form an interacting set, said method comprising: (A) coupling first and second fragments of a reporter molecule to different panel members; (B) mixing the products of (A); (C) testing for reporter molecule activity; and (D) identifying the panel members whose interaction results in said activity and which thus form an interacting set.

The invention also describes a method comprising directly or indirectly introducing different interacting molecules or interacting sets into separate cell populations and identifying an interacting pair or an interacting set that provides its host cells with a growth advantage relative to cells containing a different interacting pair of molecules or interacting set of molecules.

The invention also describes a method comprising directly or indirectly introducing different interacting molecules or interacting sets into separate cell populations and identifying an interacting pair or an interacting set that provides an optically detectable signal greater than that of cells containing a different interacting pair of molecules or interacting set of molecules.

The instant invention is also directed to a method of preparing an assay system comprising: (A) identifying a first and a second panel of molecules whose mutual interaction is desired to be tested; (B) coupling molecules of said first panel to first fragments of a reporter molecule; and (C) coupling molecules of said second panel to second fragments of said reporter molecule.

The invention is also directed to an assay system comprising a first panel of molecules coupled to first fragments of a reporter molecule and a second panel of molecules coupled to second fragments of said reporter molecule.

The present invention is also directed to a method for identifying an interacting set of molecules comprising: (A) generating fragments of a reporter molecule which have a directly or indirectly detectable activity when associated; (B) coupling first fragments to members of a first panel of molecules; (C) coupling a second fragment to a second molecule; (D) mixing the products of B) and C); (E) directly or indirectly testing for said activity; and (F) identifying the panel members whose interaction with the second molecule resulted in said activity.

The invention is also directed to a method for identifying an interacting set of molecules comprising: (A) identifying a first panel of molecules and a second molecule whose mutual interaction is desired to be tested; (B) coupling molecules of said first panel to first fragments of a reporter molecule; (C) coupling the second molecule to a second fragment of said reporter molecule; (D) mixing the products of B) and C); (E) directly or indirectly testing for said activity; and (F) identifying the panel members whose interaction with the second molecule resulted in said activity and which thus form interacting pairs.

The instant invention is also directed to a method of preparing an assay system comprising: (A) identifying a panel of molecules whose interaction with a second molecule is desired to be tested; (B) coupling molecules of said first panel to first fragments of a reporter molecule; and (C) coupling said second molecule to a second fragment of said reporter molecule.

The invention is also directed to an assay system comprising a first panel of molecules coupled to first fragments of a reporter molecule and a second molecule coupled to a second fragment of said reporter molecule.

The present invention is also directed to a method for identifying interacting molecules comprising: (A) generating fragments of a reporter molecule which have a directly or indirectly detectable activity when associated; (B) coupling the first fragment to a first molecule; (C) coupling the second fragment to a second molecule; (D) mixing the products of B) and C); and (E) directly or indirectly testing for said activity in the absence or presence of one or more chemical or biological compounds.

Within the context of the present invention a panel can be a library, which is a collection of molecules that differ from one another structurally or functionally. A panel can also be any group of molecules purposefully chosen to test their ability to closely interact, either physically, chemically, etc., with other molecules.

Within the context of the present invention a reporter molecule can be a molecule that generates a detectable signal. For example a reporter molecule can be a protein that generates a cell survival signal or a cell growth advantage or an optically detectable signal or an immunologically detectable signal. Further, a reporter molecule can be a monomeric enzyme or a multimeric enzyme, a fluorescent protein, a luminescent protein, or a phosphorescent protein.

DETAILED DESCRIPTION OF THE INVENTION

The present invention provides a very general means for in vivo screening for protein-protein interactions, for identifying the interactions involved in any biochemical process, and for validating the interactions. The invention can be used in any cell type, whether bacterial, yeast, mouse, human, plant, or other cell type. The methods provided herein can be applied to any library of natural or synthetic molecules including but not limited to peptide libraries, cDNA libraries, antibody libraries, and defined gene libraries.

Suitable reporters for PCA, their properties, and methods of engineering fragments, have been described previously by Michnick et al. (U.S. Pat. No. 6,270,964 and References therein). One strategy for selecting a PCA reporter is based on using the following characteristics: 1) A protein or enzyme that is relatively small and monomeric, 2) for which there is a large literature of structural and functional information, 3) for which simple assays exist for the reconstitution of the protein, or activity of the enzyme, both in vivo and in vitro, and 4) for which overexpression in eukaryotic and prokaryotic cells has been demonstrated.

A large number of reporters meet these criteria and are suitable for PCAs, including dihydofolate reductase (DHFR); the green fluorescent protein (GFP) from *Aequorea victoria*; luciferase; hygromycin phosphotransferase; aminoglycoside kinase (AK); XPRT; glutathione-S-transferase (GST); GAR transformylase; beta-lactamase; and numerous others. In the present application, examples are provided for a DHFR PCA and a GFP PCA, and for mutant forms of both the DHFR PCA (DHFR-I114A) and the GFP PCA (GFP-S65G/S72A/T203Y).

DHFR is an example of a selectable marker that enables both survival-selection assays and fluorescence assays either in prokaryotic or eukaryotic cells. Prokaryotic and eukaryotic DHFR is central to cellular one-carbon metabolism and is absolutely required for cell survival in both prokaryotes and eukaryotes. Specifically, it catalyzes the reduction of dihydrofolate to tetrahydrofolate for use in transfer of one-carbon units required for biosynthesis of serine, methionine, pantothenate (in prokaryotes), purines, and thymidylate. The DHFRs are small (17 to 21 kDa), monomeric proteins. The crystal structures of DHFR from various bacterial and eukaryotic sources are known and substrate-binding sites and active site residues have been determined, allowing for rational design of protein fragments. The folding, catalysis, and kinetics of a number of DHFRs have been studied extensively. The enzyme activity can be monitored in vitro by a simple spectrophotometric assay, or in vivo by cell survival in cells grown in the absence of DHFR end products. DHFR is specifically inhibited by the antifolate drug trimethoprim. As mammalian DHFR has a 12,000-fold lower affinity for trimethoprim than does bacterial DHFR, growth of bacteria expressing mDHFR in the presence of trimethoprim levels lethal to bacteria is an efficient means of selecting for reassembly of mDHFR fragments into active enzyme. mDHFR expression in cells can also be monitored by binding of fluorescent high-affinity substrate analogs for DHFR. Finally, mDHFR is used routinely to demonstrate heterologous expression of protein in transformed prokaryotic or transfected eukaryotic cells.

GFP is an example of a reporter that has become one of the most popular protein markers for gene expression. This is because the small, monomeric 238 amino acid protein is intrinsically fluorescent due to the presence of an internal chromophore that results from the autocatalytic cyclization of the polypeptide backbone between residues Ser65 and Gly 67 and oxidation of the hydroxybenzyl side chain of Tyr 66 by atmospheric oxygen, producing the final fluorescent product p-hydroxybenzylideneimidazolinone. The chromophore absorbs light optimally at 395 nm and possesses also a second absorption maximum at 470 nm. This bi-specific absorption suggests the existence of two low energy conformers of the chromophore whose relative population depends on local environment of the chromophore. A mutant Ser65Thr that eliminates isomerization (single absorption maximum at 488 nm) results in fluorescence that is 4 to 6 times more intense than the wild type. The crystal structure of GFP is known (35), which allows structure-based design of fragments for PCA. GFP is used routinely to demonstrate heterologous expression and localization of protein in transfected eukaryotic cells.

As described previously, a reporter generating a detectable signal can be used for the construction of protein-fragment complementation assays. The ability to select among a wide range of reporters allows flexibility in automation, detection mode, instrumentation, cell type, experimental protocol, sensitivity, specificity, and cost of the assay. The principle of PCA, however, is the same regardless of the choice of reporter. Cells simultaneously expressing two proteins fused to complementary fragments (F[1] and F[2]) of a reporter will generate a signal, only if the fused proteins physically interact and then bring the complementary fragments of the reporter protein into proximity where they can fold and reassemble into an active form.

With PCA, a protein-protein interaction can be detected by cell survival/growth under selective pressure, by an optically detectable signal, or any other detectable signal generated by the reporter that is chosen for the PCA. The optically detectable signals that can be generated include calorimetric, fluorescent, luminescent, and phosphorescent signals. Because a signal can be generated and quantified in a living cell, the present invention enables not only screening for protein-protein interactions, but also immediate characterization of the affinity, dynamics, and modulation of protein-protein interactions in biochemical pathways in living cells. Examples of the invention are provided for in vivo library-vs.-library screening and selection of optimized interactions; for in vivo library screening of a cDNA library to detect interactions with a bait protein; for screening a defined gene collection of full-length cDNAs in mammalian cells, using several different reporters and detection modes; and for validating the molecular interactions detected by screening.

First, the present invention describes a strategy for library-vs-library screening in intact cells based on the folding of murine enzyme dihydrofolate reductase (mDHFR) from complementary fragments (4-7). DHFR was genetically dissected into two rationally designed fragments, each of which can be fused to a library of proteins or peptides (FIG. 1A). Members of one library which heterodimerize with a member of the other library drive the reassembly of the mDHFR fragments, resulting in reconstitution of enzymatic activity (FIG. 1B). Activity is detected in vivo using an *E. coli*-based selection assay, where the bacterial DHFR is specifically inhibited with trimethoprim, preventing biosynthesis of purines, thymidylate, methionine and pantothenate, and therefore cell division. The reconstituted mDHFR, which is insensitive to the low trimethoprim concentration present in selection, restores the biosynthetic reactions required for bacterial propagation. As a result, the interaction between library partners is directly linked to cell survival and detected by colony formation. Three selection strategies were tested (EXAMPLES 1-3), each having a different level of stringency. In the lowest stringency selection, we screened two expressed libraries against each other in a single-step selection, thereby identifying all interacting polypeptide partners. In the second strategy, we increased the selection stringency by using a mutant DHFR fragment (Ile114Ala) which prevents stable reassembly of DHFR from its fragments (5) and should thus require more efficiently heterodimerizing, as opposed to homodimerizing, interacting partners to drive enzyme reconstitution. Finally, we introduced competitive metabolic selection, where clones obtained with the second strategy were pooled and passaged through several rounds of competition selection, in order to enrich for the optimally heterodimerizing partners.

EXAMPLE 1

In order to demonstrate a large-scale library-vs-library selection based on the mDHFR PCA, we screened two designed libraries of complementary heterodimeric coiled-coil forming sequences against each other. Our goal was to determine if the strategy would select interacting peptide pairs in which amino acids at the semi-randomized positions are similar to those observed in naturally-occurring or successfully designed coiled-coils which form stable heterodimers (see refs 10-12, for example). Further, it is not currently possible to predict sequences of coiled coil-forming peptides that will simultaneously have high stability and heterospecificity as well as advantageous in-vivo properties, such as resistance to proteases. In the present approach, the heterodimerizing peptides will have such characteristics by the nature of their selection. This is crucial to practical applications of optimal interacting heterodimers for in vivo studies of protein oligomerization, e.g. the design of bispecific miniantibodies (13).

Library Design. The libraries were a hybrid between GCN4 and c-Jun/c-Fos (FIG. 2), where the central, core "a"-position ($a_3$) was randomized to either N or V, with equal probability, and the recurring "e" and "g" positions were randomized to Gln (neutral), Glu (acidic), Arg or Lys (basic), each with 25% probability. This was achieved by synthesizing oligonucleotides containing synthetic codon building blocks (14). This library design allowed a number of complex optimization problems to be solved simultaneously by biological selection. At the core a-position the choice of V-V pairing, which confers higher thermodynamic stability to helix pairs, competes with N-N pairing, which confers specificity of parallel dimerization with a defined packing register and disfavors formation of antiparallel dimers and higher order oligomers (15,16). Additionally, the importance of charged residues at the "e" and "g" positions was investigated. Formation of salt bridges between these positions of opposite monomers has been crystallographically observed (17) and has been proposed to contribute to the stability of dimer formation (18-20). Additionally, the avoidance of unfavorable electrostatic interactions between same-charged residues may be more important in driving stable, specific interactions and avoiding the formation of homodimers (21). Furthermore, the energy of charged-neutral interactions has been shown to be similar to that of charged e/g-pairs in several cases (18,21). Other factors, such as contribution of e/g-residues to helix propensity and helix dipole stabilization add to the difficulty of predicting the optimal e/g-pairs in dimerization even in simple model systems. Although a restricted number of positions were semi-randomized here (4 residue types at 8 positions and 2 residue types at 1 position, resulting in $1.31 \times 10^5$ variants per library, and $1.7 \times 10^{10}$ library-vs-library combinations), a problem of extraordinary complexity was generated, making predictions of the outcome very challenging. Resolution of this problem required a powerful selection strategy, which could be rapidly performed and analyzed; to our knowledge the DHFR fragment complementation system is currently the only strategy amenable to this.

Constructs for DHFR fragment complementation: The DNA constructs encoding the N-terminal (1-107) and C-terminal (108-186) mDHFR fragments have been previously described (5). Briefly, each fragment was amplified by PCR with appropriate unique flanking restriction sites and subcloned into a bacterial expression vector (pQE-32 from Qiagen). Each plasmid encodes an N-terminal hexahistidine tag, followed by a designed flexible linker and the appropriate DHFR fragment. Unique restriction sites between the hexahistidine tag and the flexible linker allow subcloning of the desired library. After subcloning, the resulting linker between either library and DHFR fragment was: A(SGTS)$_2$STSSGI for LibA and SEA(SGTS)$_2$STS for LibB. The design of the semi-randomized libraries is illustrated in FIG. 2. Both libraries were produced using triplet-encoding oligonucleotides (14) and amplified by PCR, using primers carrying the appropriate unique restriction sites at each terminus, and the digested, gel purified products were ligated to the appropriate vector (FIG. 1). To achieve maximal library representation, the ligation mixes were individually electroporated into XL1-Blue cells and selected with ampicillin on rich medium (LB). A 2- to 7-fold over-representation of each library was obtained. The resulting colonies were pooled and the plasmid DNA purified such that supercoiled plasmid DNA was obtained for cotransformation. In order to verify that the library populations encode the designed amino acids with the expected frequency, single clones from each library were randomly picked and sequenced before selection. No statistically significant biases were detected. Seventy to 80% of each library had no mutations or frame-shifts, and thus the library-vs-library combination yielded approximately 50% correct sequence combinations. In cotransformations, the occurrence of double transformation was calculated as the number of colonies growing under selective pressure with trimethoprim (described below) divided by the number growing in the absence, when cotransformed with equal amounts of each DNA of a given, pre-selected pair.

Single-step selection. As a first step in selection of heterodimerizing leucine zippers, a single-step selection was undertaken, using the wild-type mDHFR fragments. Selection was undertaken by cotransforming the libraries LibA-DHFR[1] and LibB-DHFR[2] and plating on selective media (FIG. 1B). Selective pressure for DHFR was maintained throughout all steps by inhibiting the bacterial DHFR with trimethoprim (1 microgram per ml) in minimal medium. Ampicillin and kanamycin (100 micrograms per ml and 50 micrograms per ml, respectively) were also included in all steps to retain the library plasmids and the lacI$^q$ repressor-encoding plasmid (pRep4), respectively. Expression of the proteins was induced with 1 mM IPTG. When selecting on solid medium, growth was allowed for 45 hrs at 37° C. When selecting in liquid medium, the starting O.D. (600 nm) was either 0.0005 or 0.0001. Cells were propagated either in Erlenmeyer flasks or in a 10 liter New Brunswick fermentor, depending on the volume required to ensure adequate representation of all clones present, at 37° C. with shaking, or stirring at 250 RPM. After 10 to 24 hrs, O.D. (600 nm) reached 0.2 to 1.0 and cells were harvested. In competition selections, liquid culture was directly used to inoculate the next passage. We used BL21 cells with a transformation efficiency of no less than 5×10$^7$ transformants per microgram of DNA using 200 pg of DNA, or 2×10$^7$ transformants per microgram using 500 ng of DNA. In cotransformations, the occurrence of double transformation was calculated as the number of colonies growing under selective pressure with trimethoprim divided by the number growing in the absence, when cotransformed with equal amounts of each DNA of a given, pre-selected pair.

The single-step selection strategy applies only a low stringency of selection to the potential pairs, thus many library combinations were expected to be selected. Approximately 1.7% of the resulting ampicillin-resistant cells were doubly transformed, harboring (at least) one plasmid from each library when using 5 ng of each DNA, or 8% were doubly transformed when using 20 ng of each DNA, as seen from control transformations (calculated as described in the Experimental Protocol; data not shown). Of the doubly transformed cells which harbor no mutations or frame-shifts, approximately 35% formed colonies under selective conditions (Table 1). This result immediately demonstrates that even with relatively low stringency of selection, only a fraction of the possible combinations of the two libraries allows zipper heterodimerization leading to efficient mDHFR reassembly.

TABLE 1

Stringency of the selection steps: selecti n fact rs

| Single-step selection | Selection Factor[a] |
|---|---|
| Wt mDHFR fragments (5 or 20 ng) | 2.8 |
| I114A mDHFR fragments (5 or 20 ng) | $1.4 \times 10^2$ |

| Competition selection | Initial Diversity | Frequency of dominant Pair at P12[b] | Selection factor[a] |
|---|---|---|---|
| Competition (I114A) | $3.9 \times 10^6$ | WinZipA1-B1: 18/22 (82%) | $3.2 \times 10^6$ |
| Shuffling: WinZip-A1 + LibB-DHFR[2:11 14A] | $1.3 \times 10^5$ | WinZipA1-B2: 4/6 (67%) | $8.7 \times 10^4$ |
| Suffling: WinZip-B1 + LibA-DHFR[1] | $1.3 \times 10^5$ | WinZipA2-B1: 4/4 (100%) | $>1.3 \times 10^5$ |

[a]The selection factor in single-step selection is defined as the number of cotransformed cells plated (considering only the 50% which give combinations with no mutations or frame-shifts), divided by the number of colonies surviving under selective conditions (see Results); average of 2 independent experiments. This value must be calculated at low DNA concentrations ($\leq$20 ng of each DNA) since the multiple cotransformations occuring at high DNA concentrations mask the actual selection factor.
[b]P12 is the 12$^{th}$ round of serial cell passaging and competitive growth.
[c]The selection factor in competition selection is defined as the proportion of the dominant pair multiplied by the sequence diversity it was selected from.

Fourteen colonies resulting from two independent cotransformations were picked and the sequences encoding the zippers were determined. Even under these low stringency conditions there exist important biases in these sequences relative to the unselected ones (FIG. 2B). A reduction in same-charged e/g-pairs from 31.3% (unselected) to 19% (selected) and an increase in opposite-charged pairs from 25% (unselected) to 31% (selected) were seen. As well, a strong enrichment of N-N pairing at the core a-position (25% unselected vs 57% selected) was observed. The characteristics that have been enriched are consistent with the selection of stable leucine zipper heterodimers.

EXAMPLE 2

Use of the mDHFR Ile114Ala mutant in PCA. We repeated the single-step selection, using the Ile114Ala mutant of mDHFR (4,5) in order to increase the stringency of selection. We reasoned that only library partners that form the most stable heterodimers can compensate for the reduced ability of the mDHFR(Ile114Ala) fragments to fold into active enzyme, resulting in higher enzyme activity and growth rates. When bacteria were cotransformed with LibA-DHFR[1] and LibB-DHFR[2:I114A], we observed a 50-fold decrease in the number of colonies upon selective plating compared to the wild-type DHFR fragments (Table 1). Twenty-five colonies were picked from 3 independent cotransformations and the DNA sequences were analyzed. The increase in selectivity was concomitant with an extremely strong selection for N-N pairing at the core a-position (92%; FIG. 2B), illustrating that the specificity of in-register parallel alignment provided by N-N pairing is more highly favored under these in-vivo selection conditions than the higher stability afforded by V-V pairing. Reassembly of mDHFR from its fragments requires that in the final structure, the two fragment N-termini be brought close enough together to allow native-like refolding of DHFR (FIG. 1) (5,22). The peptide linkers that connect the library sequences to the DHFR fragments must be sufficiently flexible to allow DHFR to fold from its fragments, but not so long that any C-terminal to N-terminal orientation of the final folded leucine zipper would be allowed. As a result of this structural requirement, parallel in-register heterodimerization of the library peptides is the only configuration possible. Other biases in these sequences were also more pronounced than with the wt DHFR fragments (FIG. 2B). In particular, an additional increase in opposite-charged e/g-pairs from 31% to 37% was seen. In one case, a point-mutation resulted in a single clone (1/25) with a V-T pair at the core a-position.

EXAMPLE 3

Competition selection: Efficiency of selection. To further increase the selection pressure, we applied the principle of competition selection. We reasoned that, among selected zipper pairs, those which result in more stable heterodimerization will allow the most efficient enzyme reconstitution, leading to higher DHFR activity. If DHFR activity is limiting for growth, the higher activity should result in more rapid bacterial propagation, hence these cells would become enriched in a pool. Thereby, after sequential rounds of growth-competition, subtle differences in growth rate can be amplified, increasing the stringency of selection relative to the single-step selection.

Figure 4:
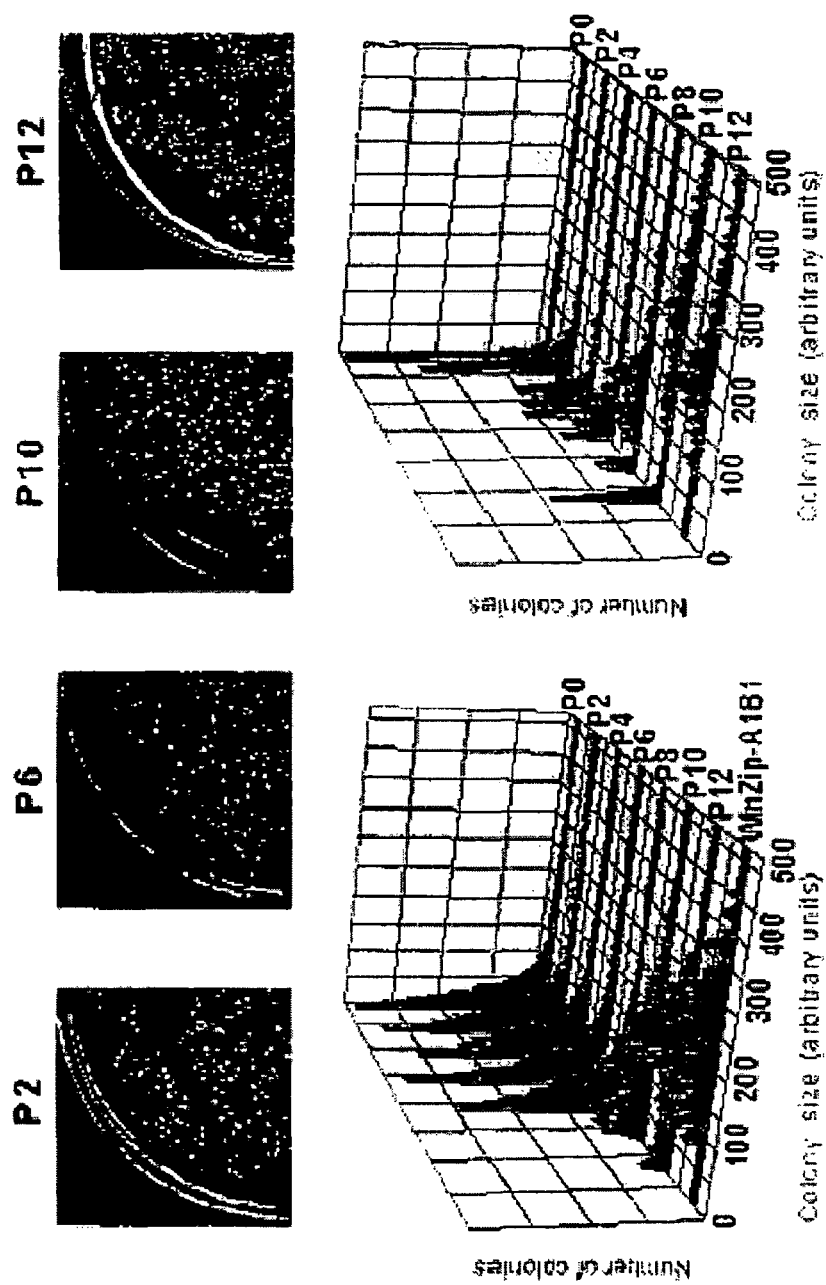
FIG. 4: Competition selection and chain shuffling. (A) Clones resulting from single-step, I114A-mutant selection were pooled (=P0) and competition selection was undertaken as described in FIG. 1C, and in the detailed description of the invention. At each passage, some cells were plated and colony sizes were quantitated. (B) Quantitation of the colony sizes from (A). For comparative purposes, quantitation of colony sizes of cells transformed with DNA of WinZip-A1B1 (but not passaged in liquid culture) is shown. (C) Quantitation of the colony sizes from passages of the chain shuffling experiment: WinZip-B1-DHFR[2:I114A]+LibA-DHFR[1].

To determine the rate at which competition can enrich for particular partner pairs, we first set up a model competition with a limited number of clones as described in FIG. 1C. The initial cell mixture (P0) contained known amounts of viable cells expressing either GCN4-DHFR[1]/GCN4-DHFR[2:I114A] or one of seven LibA-DHFR[1]/LibB-DHFR[2:I114A] pairs previously obtained in a single-step selection of those libraries, mixed at a ratio of $2.9 \times 10^4$:1 (GCN4:library clones). Productive association of the homodimeric GCN4 pair should occur only 50% of the time versus up to 100% for heterodimerizing library clones, thus is disadvantaged. When it was necessary to control precisely the starting number of cells in a competition, the number of viable cells in the starter cultures was quantitated as follows. The appropriate clones were propagated in liquid media under selective conditions and dilute aliquots were frozen at $-80°$ C. with 15% glycerol. One aliquot for each clone was thawed and plated under selective conditions, and the colonies counted after 45 hrs. The volume of cells to use for P0 was then calculated, such that each clone should be over-represented by a factor of at least 2000. Colony sizes (in FIG. 4) were evaluated using the NIH Image Particle Analysis Facility.

Figure 3:
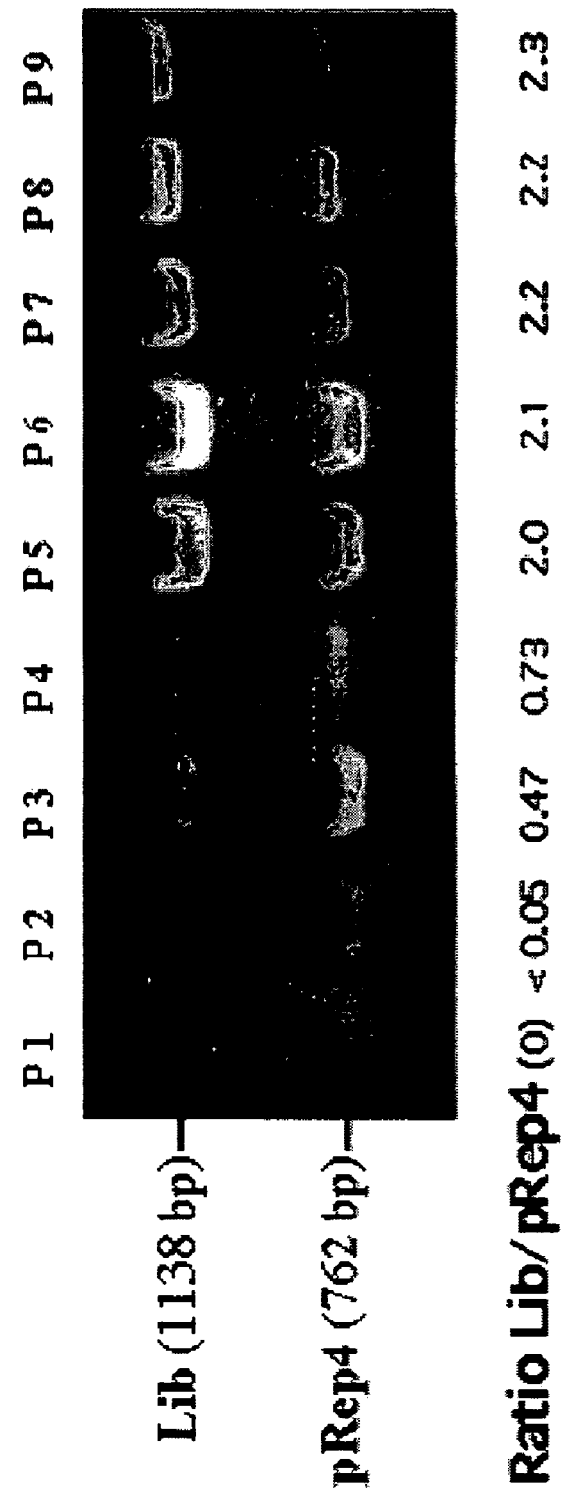
FIG. 3: Efficiency of competition in a model selection. The selection was set up by mixing known numbers of cells expressing either GCN4-DHFR[1]/GCN4-DHFR[2:I114A] fusions or one of 7 LibA-DHFR[1]/LibB-DHFR[2:I114A] pairs previously selected by single-step selection. The appearance of the library pairs in the pool was monitored by restriction analysis. A PvuII fragment (1138 bp) is unique to the LibB sequence of the LibB-DHFR[2] plasmid, while another (762 bp) is from pRep4 (repressor plasmid) and remains approximately constant. The bands were quantitated using the NIH Image gel analysis function to calculate the ratio of LibB/pRep4 (indicated below each lane).

Within 3 passages, the library pairs were already visibly enriched (FIG. 3), and after 5 passages the measured ratio between a restriction fragment indicative of the library and a constant fragment from the repressor plasmid had reached its maximium, showing that enrichment was maximal. Colonies resulting from passage 9 (P9) were sequenced. No GCN4 leucine zippers were present among 24 sequences analyzed. Therefore, enrichment of the library pairs over GCN4 by a factor of at least $24 \times 2.9 \times 10^4 = 7 \times 10^5$ was achieved. Four out of the library clones initially present survived until P9, with varying distributions (data no shown). The experiment was also repeated at a lower starting ratio of GCN4 and the same library clones were enriched, consistent with their enrichment being truly the result of selection (and not of unrepresentative sampling). This indicated that selection among the pre-selected clones was not as rapid as that seen between pre-selected and GCN4 zippers, but that the smaller differences between the pre-selected ones can still be amplified in selection. These results demonstrate that there is a direct link between reconstitution of mDHFR and growth rate.

Competition selection for optimal pairs. Our ultimate goal was to select for the "best" among the zipper pairs obtained by single-step selection. We obtained a large initial number of clones by cotransforming bacteria with 0.5 µg of DNA each from LibA-DHFR[1] and LibB-DHFR[2:I114A]. Approximately 50% of cells were at least doubly transformed (52%±10%, average of 2 independent control experiments, calculated as described in the Experimental Protocol). We obtained approximately $1.42 \times 10^4$ clones on selective medium, which arise from a $1.4 \times 10^2$-fold selection factor (see Table 1), and were thus selected from $(1.42 \times 10^4) \times (1.4 \times 10^2) = 2.0 \times 10^6$ library-vs-library cotransformants. These were pooled and passaged. There was a clear increase in colony sizes with subsequent passages, indicating that faster-growing clones were taking over (FIG. 4A, B). At P12, the colonies are homogeneously large, showing similar growth rates among the clones. Twenty-two individual colonies from P12 were picked and sequenced, as well as 11 from P10 and 2 from each previous second passage. A single pair (WinZip-A1B1, composed of WinZip-A1-DHFR[1] and WinZip-B1-DHFR[2:I114A]) was identified 18/22 times (82%) in P12, 4/11 (33%) in P10, but not in previous passages (FIG. 2C). While other sequences were found in early and late passages, none was as enriched as WinZip-A1B1. In order to verify that the growth rate recorded after competition (P12) was independent of bacteria-specific factors resulting from passaging, we cotransformed DNA from a pure clone of WinZip-A1B1 into fresh bacteria. The colony size distribution is similar for P12 and for the transformants (FIG. 4B), illustrating that the growth rate is a direct product of mDHFR reconstitution directed by the WinZip-A1B1 pair.

The sequence bias observed at the core-a position was yet stronger here: only N-N pairing was recorded at the core a-position. When the biases at the e/g-positions were calculated according to the occurrence of each sequence (n=37), there was no significant change in opposite charged pairing (37%), while a small increase in same-charged pairing was observed (from 23% to 26%) as a result of the two same-charged pair which occur in the predominant WinZip-A1B1 (FIG. 2B, C). However, when each unique sequence was considered only once (n=10) a further increase of opposite-charged e/g-pairing was observed.

EXAMPLE 4

Chain shuffling. In the above experiment, WinZip-A1B1 was selected from a sample representing $2.0 \times 10^6$ library-vs-library cotransformants. As the theoretical library-vs-library diversity is $(1.31 \times 10^5)^2 = 1.72 \times 10^{10}$, approximately 0.01% of the library-vs-library space was sampled. However, we obtained a very high coverage of either single library (theoretical complexity of $1.31 \times 10^5$), where the probability of all members being present at least once is P=0.973. Thus, each polypeptide sampled only a small portion of the opposite library ($2.0 \times 10^6/1.31 \times 10^5 = 15.4$ polypeptides of the other library with P=0.999, assuming equal transformation rates for both libraries) and it is likely that better combinations for the WinZip-A1B1 peptides may be found. Using WinZip-A1B1 as a partially optimized starting point, we combined each of the two WinZip-A1B1 polypeptides with the opposite library (WinZip-A1-DHFR[1]+LibB-DHFR[2:I114A] and WinZip-B1-DHFR[2:I114A]+LibA-DHFR[1]), as follows. DNA from the WinZip-A1B1 clone was isolated and retransformed into bacteria in order to obtain clones carrying either plasmid WinZip-A1-DHFR[1] or WinZip-B1-DHFR[2:I114A]. A pure clone (for each) was electroporated with the appropriate library. Library representation was calculated by comparison with control transformations of the same cells with DNA from the other WinZip-A1B1 polypeptide (calculated as the number of colonies growing in the presence of trimethoprim divided by the number growing in the absence). Single-step and competition selection were undertaken as described above. It should be noted that cotransformation of bacteria at high DNA concentrations (0.5 µg per library) can lead to multiple plasmid transformation, where many survivors harbor more than one of either library sequence (data not shown). However, in no case was more than one sequence pair identified per clone after any competition selection, suggesting that multiply transformed cells retained only the pair of plasmids optimal for survival throughout the competition selection.

Single-step selection yielded pre-selected pools for either competition. In both cases, the library ($1.3 \times 10^5$) was overrepresented by a factor of 24 and 14, respectively, and the probability that all members were present at least once as partners of the "constant" peptide is $P \geqq 0.999$ and 0.882, respectively. With passages of selection competition, a clear increase in colony sizes was again observed, indicating that faster-growing clones were taking over (FIG. 4C).

Figure 5:
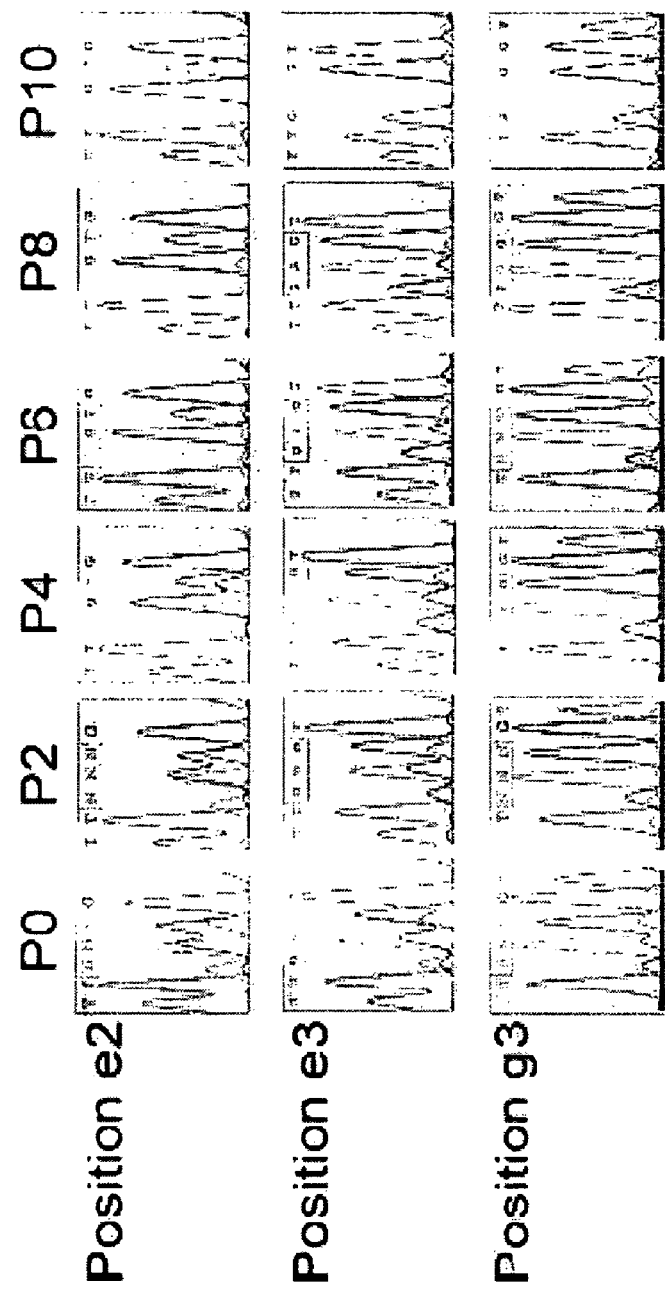
FIG. 5: Sequencing profile of pools from passages of the chain shuffling WinZip-B1-DHFR[2:I114A]+LibA-DHFR [1]. Representative semi-randomized positions (see FIG. 2) were taken from a single competition experiment, such that the selection rates can be directly compared. The ratio of the individual triplet codons (central three nucleotides of each frame) was visually estimated (CAG=Gln; GAG=Glu; AAG=Lys; CGT=Arg; the equimolar random mix of the 4 codons results in the predominance of C at the first position, A at the second and G at the third). Mixed positions are marked by (NNN), positions where a single codon is dominant ($\geq$50%) are marked in lower case and those where the codon is clear ($\geq$90%) are marked in upper case.

At P0 and each second passage, DNA from the entire pool of cells was sequenced in order to follow the rate of evolution of each library against a constant partner. FIG. 5 illustrates the results from representative semi-randomized positions. It is clear that the rate of selection is not constant at all positions: some positions showed a dominant residue ($\geqq 50\%$) already at P4 and clear selection ($\geqq 90\%$) at P6 (see position e2) while others remained mixed (<50%) until P6 and became clear only at P10 (see position g3). This was observed in both selections. The sequences from individual colonies were analyzed. In both selections, a predominant clone was identified (Table 1 and FIG. 2C), which is similar, but not identical, to the originally selected WinZip-A1B1 pair. The selection of the predominant clone WinZipA2B1 (selection of LibA-DHFR[1] against WinZip-B1-DHFR[2:I114A]) was achieved before P10, as P10 (4 clones analyzed) and P12 (4 clones analyzed) revealed only this clone. The selection of the predominant clone WinZipA1B2 (selection of LibB-DHFR[2:I114A] against WinZip-A1-DHFR[1]) was clear but not complete after 12 passages, as it was identified 4/6 times in P12 and 3/5 times in P10.

During the multiple passages performed in competition selection, the spontaneous acquisition of trimethoprim resistance by the *E. coli* DHFR could in principle lead to a "false-positive" result, where survival would be independent of the mDHFR fragment complementation. While we observed such a phenotype on one occasion at a rate of approximately 1 resistant clone per $2 \times 10^8$ bacteria in single-step selection, we never observed this in clones resulting from competition selection, although up to $10^{12}$ cells were used during each competition. Thus this phenotype does not interfere with the selection process.

We sequenced the regions N- and C-terminal to all zipper pairs obtained, including the promoter region and part of the mDHFR-fragment coding sequence (including residue 114). As well, the entire mDHFR fragment-coding sequence was verified in all WinZip clones. In no case was a mutation, rearrangement or a recombination of any constant portion of the constructs observed. In addition, all clones were subjected to restriction analysis, and showed normal restriction patterns (data not shown). As in all in vivo strategies based on fusion proteins, we cannot preclude that the selected zippers could induce folding of mDHFR from its fragments or stabilize mDHFR through interactions of the leucine zipper with either the peptide linkers or with one or both of the DHFR fragments. However, the strong selection biases we observe, particularly the perfect selection for N-N pairing under conditions of high stringency but also of complementary e-g pairings, support our hypothesis that selection is determined by heterodimerizing leucine zipper-forming peptides.

As shown above, applicants have applied the in-vivo mDHFR-fragment complementation assay to select stably interacting partners in a library-vs-library screen for heterodimerizing leucine zippers. Selection was successful both in single-step, and in competition assays. Many combinations of the two libraries were expected to form heterodimers, albeit of varying stability. The 2.8-fold selection factor observed in single-step selection using the wild-type mDHFR fragments is consistent with the expectation that many of the combinations should result in functional heterodimers, since 9 of the 10 a- and d-positions that define the hydrophobic core were invariant. Use of the I114A-mutant of mDHFR increased the stringency of selection 50-fold, and competition selection allowed amplification of the most successful pairs from this pool. The sequence biases observed indicate that selection favored N-N pairing very strongly over V-V pairing in the hydrophobic core, consistent with selection for specificity of parallel, in-register dimerization. This in-register alignment allows the direct comparison of the selected zippers as all helices are forced, by the N-N pair, to assume a parallel orientation, juxtaposing the same e- and g-residues in all selected library members. Opposite-charged e/g-pairs were generally, but not exclusively favored, suggesting that building stable zippers with good in-vivo performance is more complex than simply designing opposite-charged pairs. The increasing colony sizes observed during competition are consistent with selection based on higher levels of reconstituted mDHFR activity. Our results suggest that competition selection could be undertaken as a continuous culture in automated protein evolution schemes, and should be robust as we have observed no genetic instabilities. We efficiently isolated a predominant individual clone (WinZip-A1B1) from approximately $2 \times 10^6$ individual combinations, taken from a $10^{10}$ combinatorial space. Taken with the observed sequence biases and success in growth competition, it appears that there is a direct link between stability of zipper interaction and success in the selection process. To our knowledge, this is the first demonstration of a large-scale library-vs-library selection procedure for the optimization of protein-protein interactions.

EXAMPLE 5

PCA in Mammalian Cells

The above demonstration of the invention utilized the DHFR PCA in bacterial cells. We sought to demonstrate the utility of the DHFR PCA in mammalian cells. In addition, we sought to extend the use of PCA to cDNAs encoding mammalian proteins. First, we applied the DHFR PCA to screening for protein-protein interactions within a defined library comprising full-length cDNAs. Starting with full-length cDNAs representing proteins involved in growth factor-dependent signal transduction, genes tagged with complementary fragments of DHFR were co-transfected into mammalian DHFR-(CHO DUKX-B11) cells. Reconstitution of DHFR activity from complementary fragments allows for survival of the cells under selective pressure, thereby serving as an indicator of a protein-protein interaction.

Experimental Design. Protein-protein interactions were tested with three variations of the protein DHFR fragment fusions. First, except in specific cases, we tested the same interactions with fusions of the test proteins at either the N or C terminus of DHFR fragments. We tested these variants because, not knowing the structures of these proteins, we would not be able to predict whether the complementary DHFR fragments could be brought into proximity because the individual C or N termini of the interacting test proteins are too far from each other. Second, we tested what we call a fragment-swapping control to determine if interactions with different protein-fragment configurations (e.g., X-F[1,2] and Y-F[3] vs. Y-F[1,2] and X-F[3]) would give the same result. Finally, we tested "kinase-dead" forms of some of the protein kinases studied here. These mutants, by acting as substrate traps, are thought to bind with higher affinity to their substrates.

DNA constructs. In all cases, full-length protein-DHFR fragment fusions were expressed. We used a flexible linker peptide of 10 amino acids between the proteins and DHFR fragments, allowing us to probe interactions across distances of 80 Angstroms. The full-length cDNAs encoding PKB (Akt) and PKB (K→A), PDK1, p70S6K and p70S6K (K→A), S6 ribosomal protein, FRAP and FRAP(D→A), 4EBP1, FKBP, the alpha catalytic subunit of PP2A, and the GTPases Cdc42hs and Rac1 were amplified by PCR and subcloned into the eukaryotic expression vector pMT3 (9), in 5' or 3' of the F[1,2] and the F[3] fragment of mDHFR (4). A flexible linker consisting of (Gly.Gly.Gly.Gly.Ser)2 (SEQ. ID. NO:5) was inserted between the cDNA and the DHFR fragments as described above. The ZIP-F[1,2] and ZIP-F[3] constructs (described in: (4)) consisted of fusions with GCN4 leucine zipper-forming sequences.

DHFR survival selection assay. CHO DUKX-B11 (DHFR-) cells were split 24 hours before transfection at $8 \times 10^4$ in 12-well plates in alpha-MEM (Life Technologies) enriched with dialyzed fetal bovine serum (FBS; Hyclone) and supplemented with 10 µg/ml of adenosine, desoxyadenosine and thymidine (Sigma). Cells were transfected using Lipofectamine reagent (Life Technologies) according to the manufacturer's instructions. 48 hours after the beginning of the transfection, cells were split at approximately $5 \times 10^4$ in 6-well plates in selective medium consisting of alpha-MEM enriched with dialyzed FBS but without addition of nucleotides. Cells were observed, for the appearance of colonies, over a period of 5 to 21 days after incubation in selective medium. Only cells expressing fused interacting partners gave rise to colonies. A few surviving colonies were isolated for each transfection by trypsinizing in cloning cylinders and grown individually up to confluence.

Results. A total of 148 combinations of 35 different protein-protein interactions in growth factor-dependent signal transduction pathways were tested against each other (FIG. 6A). Growth rates for colonies of clones expressing differently oriented fusions were not significantly different, suggesting that the length of the flexible linker inserted between the gene of interest and the PCA fragment was sufficiently long to allow proteins to interact and for the DHFR fragments to be brought into proximity to fold/reassemble. Of the 35 interactions tested, 14 resulted in survival-selection with the DHFR PCA. Nine of these interactions had been identified previously. We also identified five additional interactions that had not been reported previously or had only been inferred, on the basis of indirect evidence. When we tested the substrate-trapping mutants of protein kinases, we observed no difference in the growth rates of these compared with the wild-type, active kinases. The dissociation constants for kinase-substrate interactions are low (between 10 nM and 10 micromolar) and these values are well within the range of detection of the DHFR survival PCA.

The results demonstrate the utility of the PCA strategy for the identification of known and novel protein-protein interactions in mammalian cells, and for the use of PCA with full-length cDNAs. The survival-selection assay provides a highly sensitive method for detection of protein-protein interactions in mammalian cells, as in bacterial cells. The DHFR PCA has an additional advantage in that a fluorescence assay can be constructed. Complementary fragments of DHFR, when expressed and reassembled in cells, bind with high affinity to fluorescein-methotrexate (fMTX) in a 1:1 complex. fMTX is retained in cells by this complex, whereas the unbound probe is actively and rapidly transported out of the cells. The fluorescence signal measured in the intact living cells is therefore a direct stoichiometric measure of the number of molecules of reconstituted DHFR and of the number of interacting protein complexes. Moreover, the subcellular location (e.g. membrane, cytosol or nucleus) of the protein-protein complexes can be visualized by fluorescence microscopy. We used this feature of the DHFR PCA to validate and characterize the protein-protein interactions identified in the survival-selection assay.

EXAMPLE 6

Fluorometric measurements of protein-protein interactions with DHFR PCA. CHO DUKX-B11 cells stably expressing interacting proteins fused to DHFR fragments were split at $2 \times 10^5$ in 12-wells plates in α-MEM (Life Technologies) enriched with dialyzed FBS (Hyclone) and incubated for 24 hours. Cells were washed with α-MEM and serum starved (0.5% dialyzed FBS) in α-MEM containing 10 µM fMTX (Molecular Probes) for 20 hours. Medium was removed, cells were washed, incubated in α-MEM containing 10 µM fMTX, but without serum, for 3 hours and untreated or treated with 20 µg/ml insulin (Roche Diagnostics) or 15% serum for 30 mins. For the drug treatments, after the 20 hours incubation, cells were pre-treated with 20 nM rapamycin (Calbiochem) or 300 nM wortmannin (Calbiochem) for 3 hours, and then 15% serum was added to the samples for 30 mins. For all the samples, medium was removed and the cells were washed and reincubated for 15 minutes in α-MEM (without fMTX), with addition of drugs, insulin or serum in corresponding samples, to allow for efflux of unbound fMTX. The medium was removed, cells were washed one time with PBS (phosphate-buffered saline) and gently trypsinized. Plates were put on ice and 100 µl of cold PBS was added to the cells. The total cell suspensions were transferred to 96-well white microtitre plates (Dynex) and kept on ice prior to fluorometric analysis (Perkin Elmer HTS 7000 Bio Assay Reader). Afterward, the data were normalized to total protein concentration in cell lysates (Bio-Rad protein assay).

Fluorescence microscopy. COS cells were grown on 18 mm glass cover slips to approximately $2 \times 10^5$ in DMEM (Life Technologies) enriched with 10% cosmic calf serum (CCS; Hyclone) in 12-well plates. Cells were transiently co-transfected with different combinations (as indicated) of the pMT3 plasmid harboring the full-length cDNAs fused via 10 amino acid linkers to F[1,2] or F[3], using Lipofectamine (Life Technologies). 24 hours after transfection, fMTX (Molecular Probes) was added to the cells at a final concentration of 10 µM. After an incubation of 20 hours, medium was removed and cells were washed and reincubated for 15 mins. in DMEM enriched with 10% CCS, to allow for efflux of unbound fMTX. The medium was removed and cells were washed 2 times with cold PBS and finally mounted on glass slides. Fluorescence microscopy was performed on live cells with a Zeiss Axiophot microscope (objective lens Zeiss Plan Neofluar 100×/1.30).

Figure 6B:
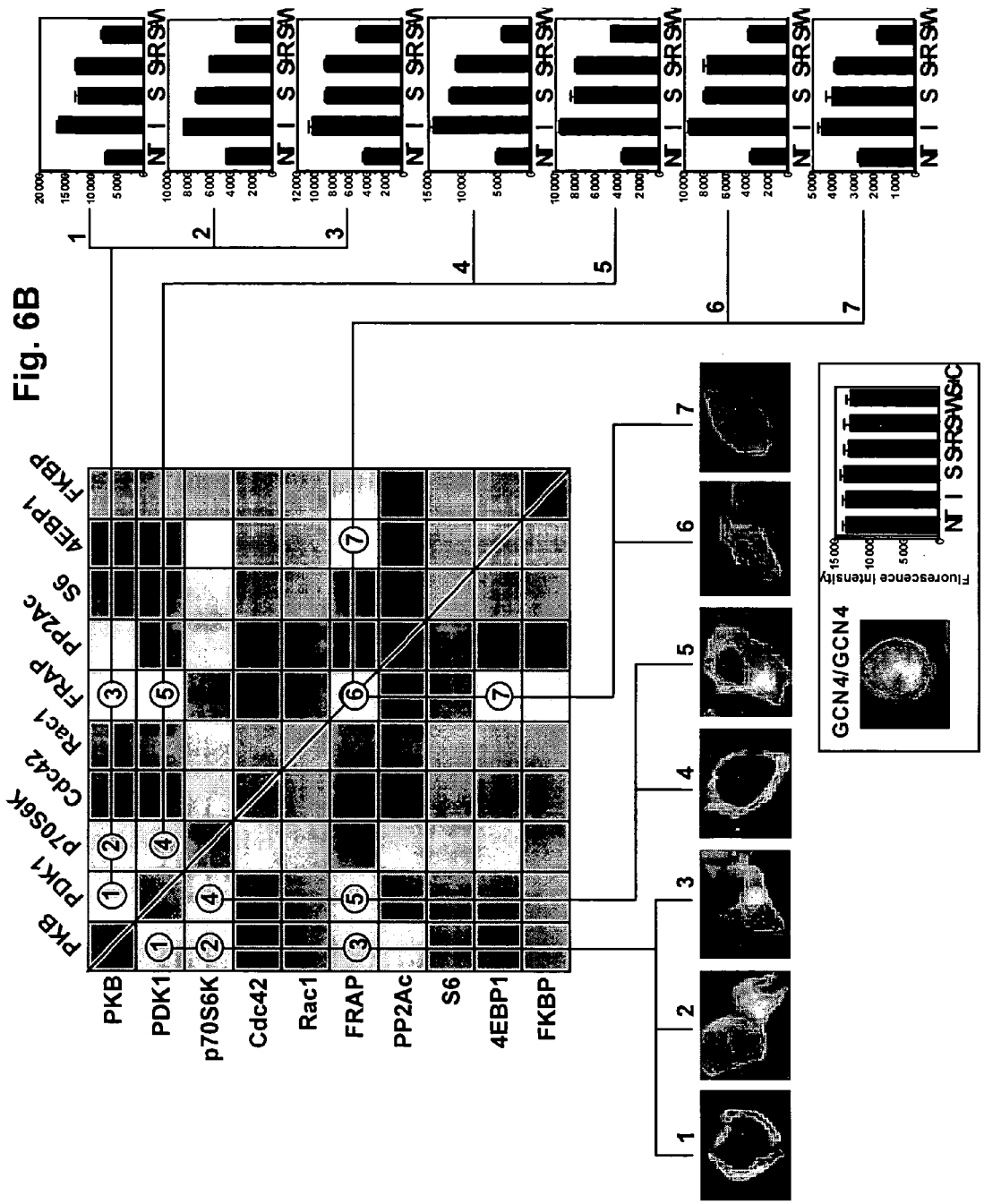
FIG. 6B. Fluorometric and microscopic analysis of interacting proteins with DHFR PCA. The grid represents selected positive (green) and negative (red) interactions observed by survival selection. The relative amount of reconstituted DHFR, a measure of the interaction between the fused protein partners, was detected by fluorometric analysis in intact cells containing seven different interacting pairs of proteins (#1-7) as indicated on the x axis: NT, no treatment; I, insulin; S, serum; R, rapamycin; W, wortmannin. Microscopy, revealing subcellular locations of protein-protein complexes, also is shown for interactions 1-7. The dimerization of GCN4 leucine zipper (GCN4/GCN4) was used as a control.

Results. FIG. 6B shows the results of total fluorescence analysis (right hand panels) and fluorescence microscopy (lower panels) of stable cell lines generated by survival-selection. For example, the protein kinase PKB formed protein-protein interactions with PDK1, with p70S6K and with FRAP, and these interactions could be detected by survival-selection (FIG. 6A) and by fluorescence (FIG. 6B) using the DHFR PCA. As shown in the photomicrographs the PKB/PDK1 complex was located at the cell membrane, whereas the PKB/p70S6K complex and the PKB/FRAP complexes were located predominantly in the cytoplasm. As shown in the histograms of fluorescence intensity (right-hand side of FIG. 6B), all three protein-protein complexes involving PKB (Panels 1-3 in FIG. 6B) were increased by treatment of the cells with insulin or serum for 30 minutes, and were decreased by treatment with wortmannin. These results are consistent with the known roles of these proteins in the growth-factor, PI3K-mediated pathways in mammalian cells (for review, see reference 37).

The examples presented herein illustrate an important feature of PCA, which is that interactions can be detected directly and between full-length proteins expressed in cells in which the proteins normally function, assuring that subcellular targeting, post-translational modifications and interactions with other proteins needed for correct functioning of the proteins can occur. Then, following identification of a protein-protein interaction, functional characterization can be carried out by using the PCA to detect perturbations of protein-protein interactions caused by agents, such as hormones or specific inhibitors or other compounds that modulate the specific biochemical pathway in which the proteins participate. In addition to quantitation of the protein-protein complex by fluorescence PCA, observations of subcellular location and induced translocation of complexes can serve as yet another functional validation criterion. Thus, the PCA screening strategy combines a simple in vivo library screening step with direct functional assays.

It is an additional feature and advantage of the invention that any of a large number of reporters can be used for the construction of the PCA, allowing flexibility in the design, detection, sensitivity and specificity of the assays. Examples of suitable reporters are provided below. It will be apparent to one skilled in the art that the present invention is not limited to the any specific reporter or its use.

Alternative Survival-Selection or Growth Reporters

In the mammalian survival selection example provided above, DHFR-cells were used such that survival-selection occurred only in the presence of an interacting pair of proteins. Alternative survival-selection PCAs can be used in the present invention, including dominant and recessive selection strategies. For example, library screening in eukaryotic cells could be performed even in cells containing a normal complement of DHFR, by growing the cells in the presence of a low level of methotrexate which is cytostatic but not cytotoxic. If a DHFR PCA is performed under these conditions, cells will grow only if two interacting proteins reconstitute an excess of DHFR activity via fragment complementation. A variety of other reporters suitable for the construction of survival-selection assays can be used in the present invention to construct assays based on dominant or recessive selection, including reporters conferring drug resistance or metabolic selection. Examples of alternative reporters for PCA include but are not limited to aminoglycoside kinase (AK), beta-lactamase, thymidine kinase, hygromycin-B-phosphotransferase, adenosine deaminase, L-histidinol NAD+ oxido-reductase, xanthine-guanine phosphoribosyl transferase (XPRT), glutamine synthetase, asparagine synthetase, puromycin N-acetyltransferase, aminoglycoside phosphotransferase, bleomycin binding protein, cytosine methyltransferase, O6-alkylguanine alkyltransferase, glycinamide ribonucleotide (GAR) transformylase, glycinamide ribonucleotide synthetase, phosphoribosyl-aminoimidazole synthetase, formylglycinamide ribotide amidotransferase, phosphoribosyl-aminoimidazole carboxamide formyltransferase, fatty acid synthease, IMP dehydrogenase, and any other selectable, metabolic, or drug resistance marker that enables cell survival or growth under specific conditions. These and similar reporters can be dissected into fragments and used in conjunction with the present invention, such that cell survive under certain conditions only if two proteins interact and reconstitute the activity of the reporter from which the fragments were derived. It will be apparent to one skilled in the art that a variety of measures of cell survival or cell growth can be employed for detection, including cell number, cell DNA content or protein content, cell size or shape, optical density, staining, and other methods.

Alternative Optically Detectable Reporters

As shown above, PCAs can be constructed to enable visualization, quantitation, and localization of protein-protein complexes. The example shown in FIG. 6B utilized DHFR as the reporter, where the reconstituted DHFR was detected by binding of fluorescein-MTX, resulting in a green fluorescent signal. It will be apparent to one skilled in the art that a variety of spectral properties can be generated with such assays. For example, as shown in FIG. 6C, a red fluorescence signal can be generated upon the interaction of two proteins simply by using a different fluorophore such as Texas Red-methotrexate in conjunction with the DHFR PCA. Therefore, a wide spectrum of fluorescence assays can be constructed, for example by using any of the BODIPY, Cy3, Cy5, rhodamine, coumarin, or other dyes conjugated to methotrexate.

DHFR exemplifies reporters which can bind a fluorescent molecule, thereby generating a fluorescent signal upon fragment complementation. Alternative reporters suitable for the present invention include other enzymes that cleave a substrate to produce a colored, fluorescent, luminescent, or phosphorescent product. For example, firefly luciferase is a 62 kDa monomeric protein which catalyzes oxidation of the heterocycle luciferin. The product possesses one of the highest quantum yields for bioluminescent reactions. Luciferase, such as from firefly or *Renilla*, provides for a PCA that is rapid, inexpensive, quantitative, and very sensitive. Beta-lactamase is a monomeric enzyme suitable for the present invention. A number of substrates for beta-lactamase are readily available, generating reaction products that can be detected calorimetrically (e.g. nitrocefin), by fluorescence (e.g. coumarin) or by a shift in fluorescence ratio from green to blue upon hydrolysis of a beta-lactam-ring (e.g. CCF2/AM). Other reporters that can be used in conjunction with the present invention include DT-diaphorase, NADH-diaphorase, glutathione-S-transferase, chloramphenicol acetyltransferase, uricase, SEAP (secreted form of human placental alkaline phosphatase, B-glucuronidase, and tyrosinase. Intrinsically fluorescent proteins such as the green fluorescent protein (GFP) from *A. victoria* or similar fluorescent proteins from a other species can be used in conjunction with this invention, thereby eliminating the need for addition of a substrate or probe for detection. Also, PCAs based on fragments of antigens or antibodies can be created and used in conjunction with simple detection schemes. For example, PCAs based on fragments of a non-native antigen could be constructed such that a protein-protein interaction results in reconstitution of an epitope that can be detected with an antigen conjugated to a detectable moiety such as biotin or fluorescein. Similarly, PCAs based on fragments of an antibody could be constructed such that a molecular interaction results in reconstitution of a functional antibody that binds to an antigen conjugated to a detectable moiety. Any of these and similar reporters can be used, and modifications thereof, in conjunction with the present invention.

EXAMPLE 7 cDNA library screening with PCA. Recent systematic large-scale applications of yeast two-hybrid screens have revealed the importance of such approaches for both identifying large numbers of novel protein-protein interactions and for applying in vivo cDNA screening approaches to achieve full coverage of a genome (i.e. ability to identify all interactions). Here we describe the use of PCA for cDNA library screening.

Specifically, we sought to identify novel proteins interacting with PKB (Akt) by screening a cDNA library using PKB (Akt) as the bait protein. Further, we sought to use fluorescence as the primary detection mode. The use of a fluorescence assay as compared with a survival-selection assay would allow library screening by fluorescence-activated cell sorting (FACS). Instead of DHFR, we used the green fluorescent protein (GFP) from *A. victoria*. As for the DHFR PCA, cells simultaneously expressing two proteins fused to complementary fragments (F[1] and F[2]) of GFP will produce a signal, only if the fused proteins physically interact and then bring the complementary fragments of the reporter protein into proximity where they can fold and reassemble into an active form. With the GFP PCA the fluorescence is autocatalyzed upon fragment complementation, eliminating the need for a fluorescent probe or exogenous substrate. We screened a human brain cDNA library containing between $10^7$ to $10^8$ independent clones, and performed the screening in transiently-transfected COS-1 cells, using PKB (Akt) as the 'bait' and using FACS to detect the fluorescence generated by protein-fragment complementation.

Screening strategy. The overall screening strategy can be schematically divided in 5 steps shown in FIG. 7. In the first step, a plasmid expressing full-length Akt fused to the C-terminal fragment of GFP (Akt-GFP[2]) is cotransfected in COS-1 cells with plasmids expressing the cDNA library prey proteins fused to the N-terminal fragment of GFP (GFP[1]-cDNAlibrary) (FIG. 7, step 1). To maximize the incorporation of large cDNAs into cells, the GFP[1]-cDNA library expression vectors were divided into four pools (fractions 1 to 4), according to the size of the inserted cDNAs. A flexible 10 amino acid linker was also inserted between the fused protein and the GFP fragments, to assure that the orientation/arrangement of the fusions in space is optimal to bring the GFP fragments into close proximity (13). A physical interaction between a cDNA expressed protein and the bait induce the reconstitution of GFP from its fragments and positive clones can be collected by fluorescence-activated cell sorting (FACS) (FIG. 7, step 2). Separate populations of cells were defined based on comparison to 1) those with higher fluorescence than untransfected cells and 2) those with higher fluorescence than those in which the GFP C-terminal fragment alone (GFP[2]) is coexpressed with the GFP[1]-cDNA library fusions. Cells were sorted with gating at P>0.001 of the false-positive background. Plasmids were then extracted from sorted cells and transformed into DH5-alpha bacterial cells, grown in the presence of ampicillin to select for only those plasmids harboring the cDNA constructs (Amp marker in the plasmid) and eliminate the Akt bait plasmid containing a chloramphenicol marker (FIG. 7, step 3). Amp-positive clones were picked, plasmids extracted (FIG. 7, step 4) and interactions of individual proteins with Akt reconfirmed by cotransfecting COS-1 cells with the Akt fusion and individual cDNA fusions (FIG. 7, step 5) and detection by FACS (FIG. 7, step 6). This last step is necessary, since an important source of contaminants in cell sorting are negative cells that are inadvertently sorted to the positive pool, even at slow sorting rates.

DNA constructs. The full-length cDNA encoding Akt1 was amplified by PCR and subcloned 5' of the F[2] fragment of GFP, into the eukaryotic expression vector pMT3 where the ampicillin resistance gene has been replaced by a chloramphenicol resistance gene, resulting in the Akt1-GFP[2] fusion expressing vector. For the construction of the GFP[1]-cDNA library fusions, a human brain cDNA library was excised from the vector pEXP1 (ClonCapture cDNA library, Clontech, Palo Alto, Calif.) using SfiI restriction sites and inserted into the pMT3 vector, 3' of the GFP[1] fragment of GFP. The GFP[1]-cDNA library fusion expression vectors were divided into four pools, according to the size of the inserted cDNAs, and amplified at 30° C. in liquid medium. GFP[1] corresponds to amino acids 1 to 158 and GFP[2] to amino acids 159 to 239 of GFP and were amplified by PCR from pCMS-EGFP (Clontech). In all the fusion constructs, a 10 amino acid flexible linker consisting of $(Gly.Gly.Gly.Gly.Ser)^2$ was inserted between the fused protein and the GFP fragments, to assure that the orientation/arrangement of the fusions in space is optimal to bring the GFP fragments into close proximity. The F[1]-GCN4 and GCN4-F[2] constructs consist of fusions with GCN4 leucine zipper-forming sequences and are used as controls. The interaction of GCN4/GCN4 leucine zippers was readily detected with the GFP PCA (FIG. 9B) as with the DHFR PCA (FIGS. 6B and 6C).

Figure 8:
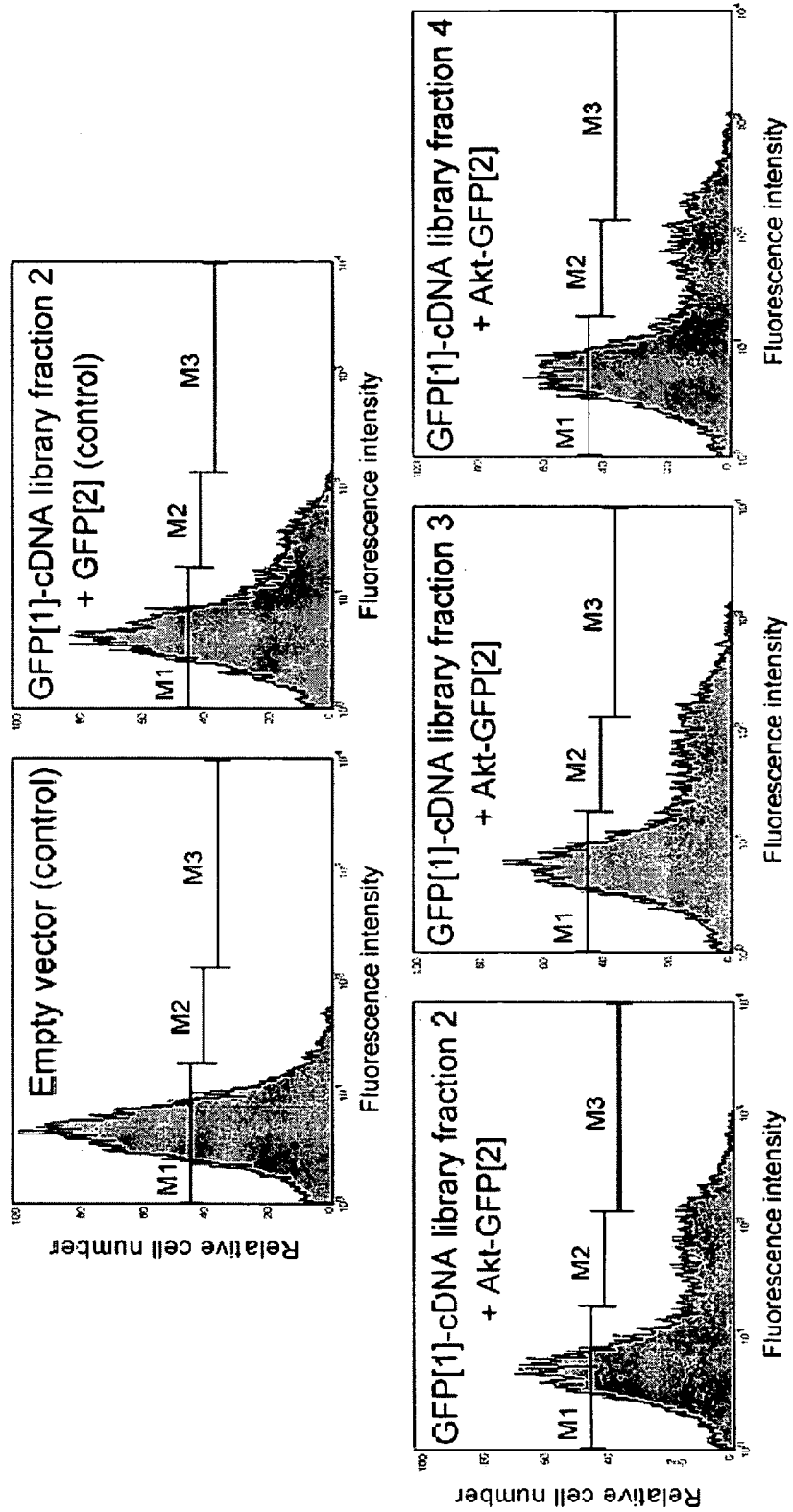
FIG. 8. First-pass screening of size pooled cDNA clones by FACS. COS-1 cells were cotransfected with the cDNA library fusions (GFP[1]-cDNA library) and the full-length Akt1 fusion (Akt1-GFP[2]) expressing vectors. Physical interactions between Akt1 and a cDNA-encoded protein induces the folding and reconstitution of GFP from its fragments, generating fluorescence. The F[1]-cDNA library fusions were transfected as several pools, according to their size. Positive clones (gate window M3) were collected by fluorescence-activated cell sorting (FACS). Controls included: (1) transfection with an empty vector and, (2) cotransfection with the GFP[1]-cDNA library fusions and the GFP[2] fragment alone (without fusion) expressing vectors.
Figure 9:
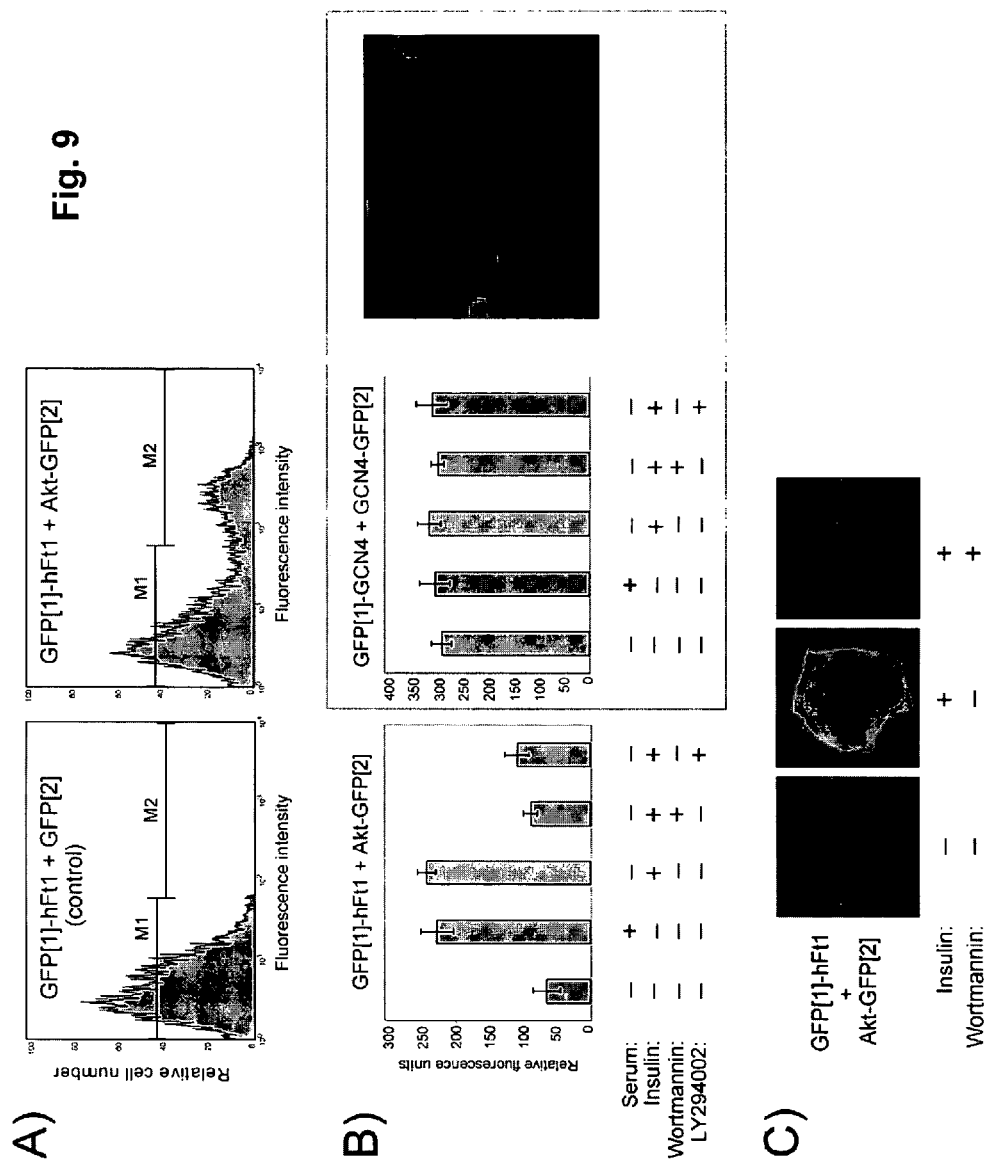
FIG. 9. Validation of a library screening hit with the GFP PCA. (A) Interaction of hFt1 with Akt1 was confirmed by co-transfecting COS-1 cells with the individual GFP[1]-cDNA fusion coding for full-length hFt1 (GFP[1]-hFt1) together with the Akt1-GFP[2] fusion, followed by FACS analysis. The physical interaction between Akt1 and hFt1 induced the folding and reconstitution of GFP from its fragments, generating a fluorescent signal (gate window M2). Cotransfection of cells with GFP[1]-hFt1 fusion and free GFP[2] expressing vectors was used as a negative control. (B) Pharmacological modulation of the Akt1/hFt1 interaction. The relative amount of reconstituted GFP, a measure of the interaction between the fused protein partners, was detected by fluorometric analysis in intact cells. The dimerization of GCN4 leucine zipper was used as a control. (C) Subcellular location of the Akt1/hFt1 protein complex in HEK293T cells treated with insulin or wortmannin as in (B).

Transfection and Fluorescence Analysis. COS-1 cells were grown in DMEM (Invitrogen, Carlsbad, Calif.) supplemented with 10% fetal bovine serum (FBS; Hyclone, Logan, Utah). COS-1 cells were plated in 150-mm dishes 24 h before transfection. Cells were transfected (10 μg DNA total/dish) using Lipofectamine reagent (Invitrogen, Carlsbad, Calif.) at around 60% confluence, with pMT3 vector harboring the human brain cDNA library fused to the F[1] fragment of GFP (GFP[1]-cDNA library) and pMT3-chloramphenicol vector containing the full-length Akt1 fused to the F[2] fragment of GFP (Akt1-GFP[2]). The GFP[1]-cDNA library fusions were transfected in several pools, according to their size. 48 h after transfection, positive clones were collected on a fluorescence-activated cell sorter (FACS) analyzer (FACScalibur, Becton Dickinson, Franklin Lakes, N.J.), with stimulation with an argon laser tuned to 488 nm with emission recorded through a 525 nm band width filter. The total DNA from each pool of positive cells was extracted (DNeasy tissue kit, Qiagen, Chatsworth, Calif.), transformed in DH5-alpha bacterial cells and plated on LB-agar containing ampicillin at 100 micrograms per ml (no propagation of the chloramphenicol-resistant vector harboring the Akt1-GFP[2] fusion). DNA plasmids containing the GFP[1]-cDNA fusions were extracted from individual clones and re-transfected separately with Akt1-GFP[2] or with F[2] alone (negative control) to discard negative clones that enter the pool during the cell sorting. After this second round of selection, the DNA plasmids corresponding to the positive clones were submitted to sequence analysis.

cDNA Library screening results. Results for the screening of fractions 2, 3 and 4 of the cDNA library are presented in FIG. 8. Fractions 2, 3 and 4 corresponded to cDNAs between 0.5 to 2 kb, 2 to 3 kb and 3 to 4.5 kb, respectively. Fraction 1 (cDNAs<0.5 kb) was not screened because it was likely to contain a large proportion of truncated cDNAs. We compared two negative controls to establish whether false-positive signals could arise due to non-specific reconstitution of GFP from its fragments. The two controls consisted of cells transfected with empty vector (FIG. 2, top left) versus cells cotransfected with GFP[1]-cDNA library fractions and GFP[2] alone (FIG. 8, top right; fraction 2 shown). Cells transfected with empty vector showed a homogeneous population (FIG. 8, top left) whereas a clear population of cells with enhanced fluorescence was detected in the case of GFP[1]-cDNA library fractions and GFP[2] alone (FIG. 8, top right), suggesting that some cDNA library members nonspecifically induce folding and reconstitution of GFP from its fragments (there is no significant spontaneous reconstitution of GFP from its fragments, as shown in FIG. 9A, left panel). We defined region of this distribution containing 5% of the cell population as gate window M2 and the region representing the upper 1% of the control fluorescence distribution as gate window M3. Positive cells (M3) were sorted by FACS and several thousand clones were recovered (FIG. 8, lower panels). The total DNA from the M3 pools of positive cells for fractions 2, 3 and 4 were separately extracted and transformed into DH5alpha bacterial cells, grown on LB-agar/ampicillin plates to select only for plasmids harboring cDNA. We obtained a total of approximately 2,500 colonies. 300 clones were picked, plasmids extracted and interaction of individual proteins with the bait (Akt) confirmed by cotransfecting individual positive GFP[1]-cDNA fusions with Akt-GFP[2] in COS-1 cells (or with GFP[2] only, as a negative control) and analysis by FACS. After this second round of selection, plasmid cDNAs for 100 of the positive clones were sequenced.

Analysis of individual cDNA clones. Among the 100 clones sequenced, 54 yielded useful data. Among these, 22 sequences corresponded to 17 genes of potential interest, while the rest were determined to have no sequence homology to a gene of known function or encoded potential false-positives. The remaining 5 sequences were eliminated on the grounds of being contaminants, coding in 4 cases for genomic sequence from macaque and 1 from adenovirus. Nine of the sequences were identified as human genomic sequence for which 5 have human ESTs but no known homologues. Most of the 17 promising hits could be linked to Akt function on the basis of evidence supporting their role in cellular functions in which Akt is implicated. These include genes involved in cytoskeletal organization, chemotaxis, and differentiation and apoptosis, particularly in brain and myocytes. Below we focus on validation of a novel cDNA that was identified three times out of the 100 clones sequenced, the human homologue of the mouse gene Ft1, which we called hFt1. The cDNA encoding hFt1 was complete in the three clones isolated.

Functional validation of screening hit. Interaction of hFt1 with Akt1 was confirmed by co-transfecting COS-1 cells with the individual GFP[1]-cDNA fusion coding for full-length hFt1 (GFP[1]-hFt1) and the Akt1-GFP[2] fusion, followed by FACS analysis. First, the Akt/hFt1 interaction was confirmed with the full-length genes by co-transfecting COS-1 cells at around 60% confluence with GFP[1]-hFt1 and Akt-GFP[2] (or with GFP[1]-hFt1 and GFP[2] alone, as a negative control) at 1 microgram total DNA/well using Lipofectamine reagent (Invitrogen, Carlsbad, Calif.) according to the manufacturer's instructions. 48 hours after transfection, COS-1 cells were gently trypsinized, resuspended in 500 µl of PBS and analyzed by FACS. The physical interaction between Akt1 and hFt1 induced the folding and reconstitution of GFP from its fragments, generating a fluorescent signal (FIG. 9A; gate window M2). Cotransfection of cells with GFP[1]-hFt1 fusion and free GFP[2] expressing vectors was used as a negative control.

We next sought to determine whether the Akt/hFt1 interaction could be modulated by agents that activate or inhibit PI3K-mediated signal transduction pathways, of which Akt is a downstream effector. As demonstrated above with the DHFR PCA for the interactions of PKB (Akt) with PDK1, p70S6K, and FRAP (FIG. 6B), protein-protein interactions that occur within a specific biochemical pathway can be modulated in predicted ways by agents that activate or inhibit the pathway. We applied a similar strategy to the newly discovered Akt/hFt1 interaction, in this case using the GFP PCA in human cells. HEK293T cells were split in 12-well plates 24 h before transfection. 24 h after transfection, cells were washed with PBS and serum-starved overnight in medium containing 0.5% FBS. The next day, cells were untreated or treated with 300 nM wortmannin or 50 micromolar LY294002 (Calbiochem, San Diego, Calif.) for the last hour. Afterward, cells were stimulated for 30 min with 10% serum or 20 microgram per ml insulin (Roche Diagnostics, Indianapolis, Ind.), washed with PBS, gently trypsinized and resuspended in 200 microliters of PBS. The total cell suspensions were transferred to 96-well black microtiter plates (Dynex; VWR Scientific, Mississauga, Ontario) The relative amount of reconstituted GFP, a measure of the interaction between the fused protein partners, was detected by fluorometric analysis (Spectra MAX GEMINI XS, Molecular Devices, Sunnyvale, Calif.), using an excitation wavelength of 488 nm, emission of 525 nm and a cut-off filter of 495 nm. Afterward, the data were normalized to total protein concentration in cell lysates (Bio-Rad protein assay, Hercules, Calif.). The background fluorescence intensity corresponding to non-transfected cells was subtracted from the fluorescence intensities of all of the samples. The results are shown in FIG. 9B. Fluorescence intensity is given in relative fluorescence units (y axis); error bars represent standard errors of the mean calculated from three independent samples. As shown for other Akt interactions in mammalian cells, the Akt/hFt1 interaction was significantly enhanced after treatment of HEK293T cells with serum or insulin, while both wortmannin and LY294002 inhibited insulin-induced stimulation of the interaction (FIG. 9B, left panel). These patterns of stimulation and inhibition are consistent with protein-protein interactions activated through PI3K-associated signaling pathways. The cell treatments did not alter protein-protein interactions in a non-specific way as shown by the lack of treatment effect on the dimerization of GCN4 leucine zippers (FIG. 9B, right panel).

As an additional validation step, we examined the subcellular location of the Akt/hFt1 complex and changes in location following perturbation of the PI3K pathway in vivo. For fluorescence microscopy, HEK293T cells were grown on 18-mm glass cover slips prior to transfection. Cells were cotransfected with GFP[1]-hFt1 and Akt1-GFP[2] and treated with insulin or wortmannin as for FIG. 9B. Cells were washed twice with PBS and mounted on glass slides. Fluorescence microscopy was performed on live cells (Nikon TE2000U, FITC filter, objective lens 100×). The interaction between Akt and hFt1 occurred predominantly at the plasma membrane in insulin-stimulated cells and appeared to be both disrupted and to dissociate from the membrane after treatment of cells with wortmannin (FIG. 9C). A first step in activation of Akt is its recruitment to the plasma membrane via interaction of its N-terminal PH domain with PIP3 lipids that themselves are synthesized by PI3K activities. Thus, the results suggest that the hFt1 interaction with Akt may occur at the membrane or be recruited to the membrane with Akt as part of an Akt activation complex.

These results illustrate the complete cycle of functional cloning by a GFP PCA strategy, from FACS to first-pass functional validation. Compared with yeast two-hybrid methods, PCA has the advantage of providing a straightforward in vivo cDNA library screen with quantitative functional assays that provide initial validation of the cDNA products as being biologically relevant. The screening steps are easily scalable and in principle, tens of thousands of clones could be isolated in a few hours by applying automation to the follow-up steps of cloning, colony picking, DNA isolation and sequencing.

EXAMPLE 8

As shown above with the DHFR PCA, mutations can be engineered into PCA fragments in order to fine-tune the assay properties. A large number of mutations have been described for GFP that confer changes in signal intensity, excitation and emission maxima, and other properties of the fluorophore. In the case of the GFP PCA we created mutant fragments in order to increase the signal intensity. We introduced the mutations S65G, S72A and T203Y (36) into GFP[1] and GFP[2] (described above) by PCR. In the intact fluorescent protein, these mutations correspond to the GFP variant known as enhanced yellow fluorescent protein ("EYFP") which is often simply referred to as YFP (35). With intact GFP, the introduction of these mutations results in a protein with excitation and emission maxima at 514 nm and 527 nm, respectively, in which the chromophore matures fourfold faster than for the wild type protein, generating a brighter signal. The YFP reporter fragments (YFP[1] and YFP[2]) were cloned into pcDNA3.1Z (Invitrogen, Carlsbad, Calif.) expression vector.

We first tested the YFP PCA with full-length cDNAs encoding PKB (Akt) and PDK1 (PDPK1). We previously showed an interaction of Akt with PDK1, using the DHFR PCA in mammalian (CHO DHFR-) cells, by survival-selection and fluorescence (FIGS. 6A and 6B). To compare the YFP PCA results in human cells, full-length Akt and PDK1 were subcloned into the YFP vectors generating Akt1-YFP[1] and YFP[2]-PDK1. HEK293T cells were transfected in duplicate with 300 ng of each construct, and plated in selective medium (MEM-alpha plus 1 mg/ml Zeocin) 24 or 48 hours after transfection. Viable colonies were evaluated for fluorescence 26 days post transfection; clones showing visible membrane localization (as visualized by fluorescence microscopy) were expanded and evaluated further. Cells from AKT:Pdk1 clone 2 were seeded at $2 \times 10^4$ per well in a 96 well poly lysine coated black wall plate (Greiner) 24 hours prior to drug treatment. Cells were serum starved (0.25% serum) overnight, then stimulated with 15% serum, plus or minus 300 nM wortmannin for 2 hrs. Cells were subsequently fixed with 4% formaldehyde then treated with 10 micromolar DRAK5 to stain the nuclei prior to image acquisition by automated microscopy (Discovery-1 imaging system, Universal Imaging), using a 20× objective, and the YFP and Cy5 filter sets. A minimum of four images were collected for each treatment regime and subsequently processed to calculate the mean fluorescence intensity for the PCA in response to each treatment. Briefly, for each image, the mean pixel intensity is determined by calculating the fluorescence intensity per pixel, then dividing by the total number of positive pixels. For each treatment, the data from each image is averaged to generate a single value as shown (FIG. 10, Panel B) upon which appropriate statistical tests can be performed. FIG. 10 shows the subcellular location and fluorescence intensity generated by the Akt/PDK1 interaction in the absence and presence of wortmannin. The complex between Akt and PDK1 occurred predominantly at the plasma membrane in stimulated cells and appeared to be both disrupted and to dissociate from the membrane after treatment of cells with wortmannin, in a manner identical to that previously observed for the Akt/PDK1 complex with the DHFR PCA. Treatment with wortmannin also caused a decrease in fluorescence of the Akt/PDK1 complex (see FIG. 10, panel B), as shown previously for Akt/PDK1 with the DHFR PCA.

In vivo cDNA screening approaches potentially allow full coverage of a genome (i.e. ability to identify all possible interactions). However, the use of full-length cDNA libraries or gene collections could potentially reduce the false-positive and false-negative rates of library screening. Expression of full-length genes enables correct subcellular targeting and post-translational modifications of the expressed protein, resulting in a greater likelihood of identifying biologically relevant protein interactions. Libraries of full-length genes have been assembled by functional cloning or sequence-directed cloning to generate gene families focused on specific target classes, such as kinases (the "kinome") and GPCRs. Such full-length libraries and gene collections are increasingly available as a result of a variety of public and private genomics projects, making this approach possible on a large scale.

EXAMPLE 9

We next used the YFP PCA described above to develop a semi-automated method for large scale screening of protein-protein interactions in 96-well plates with fluorescence detection, starting with a defined full-length gene collection.

The full coding sequences for full-length genes from an internal library of interest were amplified by PCR from sequence verified full-length cDNAs. Resulting PCR products were column purified, digested with appropriate restriction enzymes to allow directional cloning, and fused in-frame to either the 5' or 3'-end of YFP[1] or YFP[2] through a linker encoding a flexible amino acid peptide as described above. Recombinants in the host strains DH5-alpha (Invitrogen, Carlsbad, Calif.) or XL1 Blue MR (Stratagene, La Jolla, Calif.) were screened by colony PCR, and clones containing inserts of the correct size were subjected to end sequencing to confirm the presence of the gene of interest and in-frame fusion to the appropriate reporter fragment. A subset of fusion constructs were selected for full-insert sequencing by primer walking. Glycerol stocks were rearrayed and inoculated into 1.2 ml SuperBroth in 96-well blocks and grown for 18 hours at 37° C. DNAs were isolated using Qiagen Turbo BioRobot Prep kits (Qiagen, Chatsworth, Calif.) on a Beckman FX robotic workstation (Beckman Coulter, Fullerton, Calif.). Isolated DNAs were quantitated on a SpectraMax spectrophotometer (Molecular Devices, Sunnyvale, Calif.), and then normalized to a concentration of 50 ng/microliter. Concurrently, quality control (QC) routines were performed by PCR to confirm the insert size and reporter fragment of each clone (e.g. YFP[1] vs. YFP[2]), and that no cross-contamination had occurred during the growth or subsequent processing. Only DNAs with the correct insert size and reporter, no sign of contamination, and DNA concentrations of ≧50 ng per microliter were included in the pooling scheme. The location of each construct DNA within the 96-well plates, and the corresponding QC data for each construct were stored in a relational database. Pairs of construct DNAs were pooled in 96-well format on the Beckman FX workstation. Control DNAs were isolated using Qiagen Maxi-prep kits, QC'd and diluted as for the other constructs, and added to pre-determined locations in each pooled construct plate.

Fluorescence Assay and Data Analysis.

HEK293E cells (293-EBNA, Invitrogen) were maintained in MEM-alpha (Invitrogen) supplemented with 10% fetal bovine serum (Gemini Bioproducts) and 250 micrograms per ml G418 (Invitrogen). Each well of a 96-well poly-lysine coated plate was seeded with 15,000 HEK293E cells 24 hours prior to transfection. Cells were transfected with 100 ng of each DNA pool (50 ng of each fusion construct) per well with FuGene transfection reagent (Roche Diagnostics, Indianapolis, Ind.), using conditions recommended by the manufacturer. All transfections were performed in triplicate. Each 96-well plate to be assayed contained three negative controls (no DNA, a single PCA construct, and a negative PCA pair), and one positive control (a PCA pair of the NFkappaB heterodimer p50 and p65) in addition to 28 PCAs representing different pairs of cDNAs to be tested for a protein-protein interaction. Forty-eight hours after transfection, the cells were stained with a 1:300 dilution of Hoescht 33342 (Molecular Probes, Eugene, Oreg.) for 10 minutes, then washed several times with Dulbecco's phosphate buffered saline, then overlaid with a small volume of Hank's Buffered Salt Solution. After a 90 minute incubation at 37° C., mean fluorescence intensity data for each well were acquired on a SpectraMax Gemini XS Platereader (Molecular Devices), using an excitation wavelength of 485 nm, emission of 527 nm and cutoff of 515 nm. FIG. 11 shows the results of a representative 96-well microtiter plate assay. The y-axis shows the mean fluorescence intensity measurement for each PCA, with error measurements plotted as 95% confidence intervals. The positive control was p65/p50 and the negative control was PDK2/PDK2. For each plate, the negative controls are highlighted in red and the positive control in yellow. Interactions that were statistically different from the negative control are color-coded as in the legend, indicating the level of statistical significance associated with each measurement, as determined by the Student t-test of the mean fluorescence.

Immediately after measuring the fluorescence intensity on the plate reader, images were acquired from the same 96-well plates by automated microscopy (Discovery-1 imaging system, Universal Imaging) using the 10× objective, and DAPI and FITC filter sets. The Hoechst-stained cells of a control well (cells stained blue in FIG. 11, panel B) were used to establish the appropriate focal plane for image acquisition across the entire plate. Images were then acquired at two sites in each well, using a 10× objective at wavelengths appropriate for Hoechst and YFP, respectively. Representative microscopic images of the positive and negative assay controls, as well as a 'novel' positive, are shown in FIG. 11. Information can be obtained regarding subcellular locations of protein-protein complexes, as can be seen with the predominantly cytoplasmic localization of a 'novel' protein-protein interaction.

The results of the large-scale screen are shown in FIGS. 12-15. FIG. 12 shows the results depicted as a gene-by-gene matrix, with positive and negative interactions shaded in green and red, respectively (results that were not tested are in black). FIG. 13 shows the summary statistics obtained from the screen. A total of 29,793 individual assays were performed, representing triplicate analyses of 9,931 potential interactions. Since a large number of interactions were tested in multiple gene/fragment orientations, this represented 5,773 potential unique interactions. 61.4% of the potential unique interactions gave a negative result, and 12% gave a result that was discordant between fluorometric and microscopic analysis (for example, a result that was positive by microscopy but not statistically significant by plate reader was scored as discordant). The remaining assays were positive, both by plate reader and microscopy, at $p<=0.05$. Positive and negative assay controls, single DNA constructs, and mock transfections (no DNA) were analyzed a total of 459 times to determine assay reproducibility (FIG. 14). The negative assay control gave a negative result 98.3% of the time and the positive control gave a positive result 95% of the time. Excluding partial and discordant data, the true positive rate was 98.6% and the true negative rate was 99.9%. These results showed that the semi-automated screening method was highly reproducible from plate to plate and from day to day.

Figure 15:
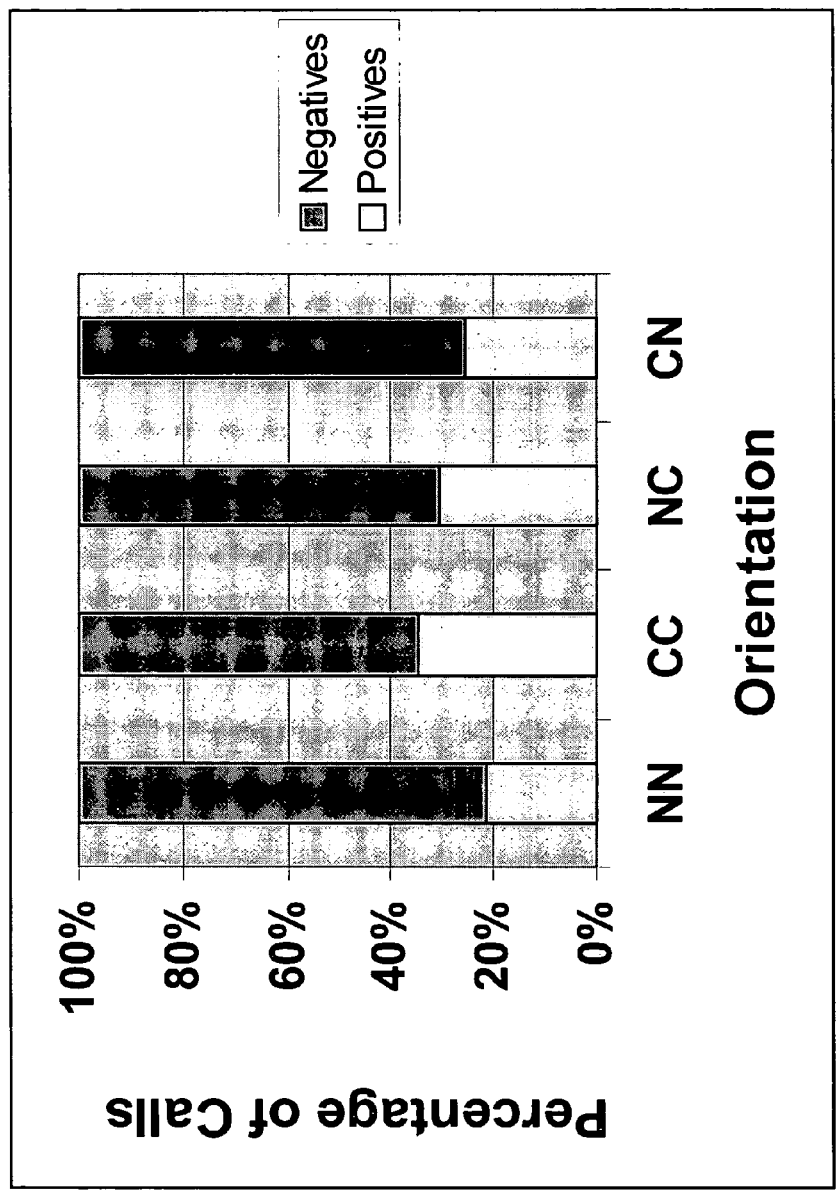
FIG. 15. Distribution of positive and negative screening results by orientation. N or C refers to the orientations of the two expressed proteins relative to the reporter fragments (N, protein is N-terminal to the fragment; C, protein is C-terminal to the fragment).

We also examined the effect of N- and C-terminal fragment orientations on the screening results, where N or C refers to the location of the protein of interest relative to the fragment. Although individual protein-protein interactions often showed a preference for one or more orientations, there was no significant overall effect of fragment orientation on the percentage of positive or negative interactions (FIG. 15). Taken together, the results suggest that PCA provides a robust, semi-automated, high-throughput approach to screening for protein-protein interactions with fluorescence detection. Moreover, the assays resulting from the screens can be used directly to validate the interactions obtained by applying quantitative and image-based analyses of the protein-protein complexes, as described herein.

These results also demonstrate that the properties of the PCA can be tailored to the assay requirements, for example, by engineering useful mutations into the PCA fragments. It will be apparent to one skilled in the art that any useful reporter can be engineered in such a fashion to create a PCA that will satisfy a particular assay format and assay specification. For example, any number of alternative mutant fluorescent proteins can be used in the present invention including any of the YFP, CFP, BFP, and RFP variants of GFP from *A. victoria*; and other fluorescent proteins from other species including *Anemonia, Discosoma* and *Renilla*; and engineered variants of the proteins that incorporate useful properties.

Furthermore, any or all of the PCAs described herein can be used to screen for protein-protein interactions and to determine the amount and subcellular location of protein-protein complexes in response to cell treatments. The DHFR PCA has the advantage of automatically generating a stable cell line as a result of cell survival and colony formation in cells expressing interacting proteins, and then enabling the same cell line to be used in biologically validating the interaction by fluorescence. However, the fluorescent protein PCAs have the advantage of not requiring the addition of a fluorescent reagent for detection, thereby reducing the number of assay steps and facilitating automation.

Alternative Embodiments of the Invention

Applicants have demonstrated that PCA enables the systematic screening for protein-protein interactions in a high throughput mode. The present invention enables a very general means of screening for interacting molecules, including peptides, proteins, or protein domains, and for immediately identifying and biologically validating protein interactions involved in any cell type or biological context. It should be understood that the present invention should not be limited to the PCAs presented herein, as these are only non-limiting embodiments of protein-fragment complementation assays. Moreover, the PCAs should not be limited in the context in which they can be used. The methods that are the subject of the present invention can be applied to any cell type or origin, whether prokaryotic or eukaryotic, including bacteria, yeast, fungus, insect, zebrafish, frog, mouse, human, and plant cells. The methods that are the subject of the present invention can also be used in conjunction with any detection method including cell growth, cell survival, cell death, viral plaque assays, calorimetric detection, fluorescent detection, luminescent detection, phosphorescent detection, immunologic detection, and/or other detection methods. The methods that are the subject of the present invention can also be applied to any reporter including any monomeric enzyme, dimeric enzyme, multimeric enzyme, fluorescent protein, luminescent protein, phosphorescent protein, antibody, or antigen. The methods that are the subject of the present invention can also be applied to any molecule whose interaction is desired to be tested, including any protein, nucleic acid, lipid, carbohydrate, small molecule, biological molecule, or other chemical entity. The methods that are the subject of the present invention can also be applied in conjunction with any experimental protocol, instrumentation platform, assay format, transfection protocol, expression vector, automation system, optical system, data collection system, database, and/or software algorithm. The methods that are the subject of the present invention can also be applied either in vivo—in living cells, embryos, tissues, or whole animals—or in vitro. The methods that are the subject of the present invention can also be applied to any library or panel of molecules, including peptide or polypeptide, DNA or cDNA, RNA or siRNA, antibody or single-chain antibody, small-molecule, natural product, and other libraries.

REFERENCES

The entire contents including the cited references of the following patents and publications are incorporated by reference in their entirety for all purposes to the same extent as if each individual patent, patent application or publication were so individually denoted.

| | |
|---|---|
| 6,270,964 | Michnick, et al. |
| 6,294,330 | Michnick, et al. |
| 6,428,951 | Michnick, et al. |

1. Fields, S. & Song, O. 1989. A novel genetic system to detect protein-protein interactions. *Nature* 340, 245-246.
2. Chien, C. T., Bartel, P. L., Sternglanz, R. & Fields, S. 1991. The two-hybrid system: a method to identify and clone genes for proteins that interact with a protein of interest. *Proc. Natl. Acad. Sci. U S A* 88, 9578-9582.
3. Smith, G. P. 1985. Filamentous fusion phage: novel expression vectors that display cloned antigens on the virion surface. *Science* 228, 1315-1317.
4. Pelletier, J. N., Remy, I. and Michnick, S. W. (1998). Protein-Fragment Complementation Assays: a General Strategy for the in vivo Detection of Protein-Protein Interactions. *Journal of Biomolecular Techniques*, 10: 32-39.
5. Pelletier, J. N., Campbell-Valois, F. X. & Michnick, S. W. 1998. Oligomerization Domain-Directed Reassembly of Active Dihydrofolate Reductase From Rationally Designed Fragments. *Proc. Natl. Acad. Sci. USA* 95, 12141-12146.
6. Remy, I. & Michnick, S. W. 1999. Clonal Selection and In Vivo Quantitation of Protein Interactions with Protein Fragment Complementation Assays. *Proc Natl Acad Sci U S A* 96, 5394-5399.
7. Remy, I., I. A. Wilson, and S. W. Michnick 1999. Erythropoietin receptor activation by a ligand-induced conformation change. *Science* 283, 990-993.
8. Sydor, J. R., Engelhard, M., Wittinghofer, A., Goody, R. S. & Herrmann, C. 1998. Transient kinetic studies on the interaction of Ras and the Ras-binding domain of c-Raf-1 reveal rapid equilibration of the complex. *Biochemistry* 37, 14292-14299.
9. Chen, J., Zheng, X. F., Brown, E. J. & Schreiber, S. L. 1995. Identification of an 11-kDa FKBP12-rapamycin-binding domain within the 289-kDa FKBP12-rapamycin-associated protein and characterization of a critical serine residue. *Proc. Natl. Acad. Sci. U S A* 92, 4947-4951.
10. O'Shea, E. K., Lumb, K. J. & Kim, P. S. 1993. Peptide 'velcro': Design of a heterodimeric coiled coil. *Current Biology* 3, 658-667.
11. Jelesarov, I. & Bosshard, H. R. 1996. Thermodynamic characterization of the coupled folding and association of heterodimeric coiled coils (leucine zippers). *J. Mol. Biol.* 263, 344-358.
12. Zhou, N. E., Kay, C. M. & Hodges, R. S. 1994. The role of interhelical ionic interactions in controlling protein folding and stability. De novo designed synthetic two-stranded alpha-helical coiled-coils. *J. Mol. Biol.* 237, 500-512.
13. Müller, K. M., Arndt, K. M., Strittmatter, W. & Plückthun, A. 1998. The first constant domain ($C_H1$ and $C_L$) of an antibody used as heterodimerization domain for bispecific miniantibodies. *FEBS Lett.* 422, 259-264.
14. Virnekas, B., Ge, L., Plückthun, A., Schneider, K. C., Wellnhofer, G. & Moroney, S. E. 1994. Trinucleotide phosphoramidites: ideal reagents for the synthesis of mixed oligonucleotides for random mutagenesis. *Nucleic Acids Res.* 22, 5600-5607.
15. Zeng, X., Herndon, A. M. & Hu, J. C. 1997. Buried asparagines determine the dimerization specificities of leucine zipper mutants. *Proc. Natl. Acad. Sci. U S A* 94, 3673-3678.
16. Lumb, K. J. & Kim, P. S. 1995. A buried polar interaction imparts structural uniqueness in a designed heterodimeric coiled coil. *Biochemistry* 34, 8642-8648.
17. O'Shea, E. K., Klemm, J. D., Kim, P. S. & Alber, T. 1991. X-ray structure of the GCN4 leucine zipper, a two-stranded, parallel coiled coil. *Science* 254, 539-544.
18. Zhou, N. E., Kay, C. M. & Hodges, R. S. 1994. The net energetic contribution of interhelical electrostatic attractions to coiled-coil stability. *Protein Eng.* 7, 1365-1372.
19. Monera, O. D., Kay, C. M. & Hodges, R. S. 1994. Electrostatic interactions control the parallel and antiparallel orientation of alpha-helical chains in two-stranded alpha-helical coiled-coils. *Biochemistry* 33, 3862-3871.
20. John, M., Briand, J. P., Granger-Schnarr, M. & Schnarr, M. 1994. Two pairs of oppositely charged amino acids from Jun and Fos confer heterodimerization to GCN4 leucine zipper. *J. Biol. Chem.* 269, 16247-16253.
21. Lumb, K. J. & Kim, P. S. 1995. Measurement of interhelical electrostatic interactions in the GCN4 leucine zipper. *Science* 268, 436-439.

22. Buchwalder, A., Szadkowski, H. & Kirschner, K. 1992. A fully active variant of dihydrofolate reductase with a circularly permuted sequence. *Biochemistry* 31, 1621-1630.
23. Hu, J. C., O'Shea, E. K., Kim, P. S. & Sauer, R. T. 1990. Sequence requirements for coiled-coils: analysis with lambda repressor-GCN4 leucine zipper fusions. *Science* 250, 1400-1403.
24. Zeng, X., Zhu, H., Lashuel, H. A. & Hu, J. C. 1997. Oligomerization properties of GCN4 leucine zipper e and g position mutants. *Protein Sci.* 6, 2218-2226.
25. Spada, S. & Plückthun, A. 1997. Selectively infective phage (SIP) technology: a novel method for in vivo selection of interacting protein-ligand pairs. *Nat. Med.* 3, 694-696.
26. Rudert, F., Woltering, C., Frisch, C., Rottenberger, C. & Ilag, L. L. 1998. A phage-based system to select multiple protein-protein interactions simultaneously from combinatorial libraries. *FEBS Lett.* 440, 135-140.
27. Bartel, P. L., Roecklein, J. A., SenGupta, D. & Fields, S. 1996. A protein linkage map of *Escherichia coli* bacteriophage T7. *Nat. Genet.* 12, 72-77.
28. Fromont-Racine, M., Rain, J. C. & Legrain, P. 1997. Toward a functional analysis of the yeast genome through exhaustive two-hybrid screens. *Nat. Genet.* 16, 277-282.
29. SenGupta, D. J., Zhang, B., Kraemer, B., Pochart, P., Fields, S. & Wickens, M. 1996. A three-hybrid system to detect RNA-protein interactions in vivo. *Proc. Natl. Acad. Sci. USA* 93, 8496-8501.
30. Arndt, K. M., Pelletier, J. N., Müller, K. M., Michnick, S. W. and Plückthun, A. (2000). A heterodimeric Coiled-coil Peptide Pair Selected in Vivo from a Designed Library-versus-Library Ensemble *J Mol Biol*, 295: 627-639.
31. Pelletier, J. N., Arndt, K. M., Plückthun, A. and Michnick, S. W. (1999). An In Vivo Library-versus-Library Selection of Optimized Protein-Protein Interactions. *Nat Biotechnol*, 17: 683-690.
32. Pelletier, J. N., Remy, I. and Michnick, S. W. (1998). Protein-Fragment Complementation Assays: a General Strategy for the in vivo Detection of Protein-Protein Interactions. *Journal of Biomolecular Techniques*, 10: 32-39.
33. J. N. Pelletier and S. W. Michnick. (1997) A Strategy for Detecting Protein-Protein Interactions in vivo Based on Protein Fragment Complementation. *Protein Engineering*, 10(Suppl.): 89.
34. Michnick, S. W., Remy, I., C.-Valois, F. X., Vallee-Belisle, A., Galarneau, A. and Pelletier, J. N. (2000) Detection of Protein-Protein Interactions by Protein Fragment Complementation Strategies, Parts A and B (John N. Abelson, Scott D Emr and Jeremy Thorner, editors) *Methods in Enzymology*. 328, 208-230.
35. Ormo M, Cubitt A B, Kallio K, Gross L A, Tsien R Y, Remington S J. 1996. Crystal structure of the *Aequorea victoria* green fluorescent protein. *Science* 273, 1392-1395.
36. Tsien, R. 1998. The green fluorescent protein. *Annu. Rev. Biochem.* 67, 509-544.)
37. Avruch, J. 1998. Insulin signal transduction through protein kinase cascades. Mol. Cell. Biochem. 182: 31-48.
38. Remy, I., Pelletier, J. N., Galarneau, A. and Michnick, S. W. (2002). Protein Interactions and Library Screening with Protein Fragment Complementation Strategies. in: *Protein-protein interactions: A molecular cloning manual*. E. A. Golemis, editor. Cold Spring Harbor Laboratory Press. Chapter 25, 449-475.

---

What we claim is:

1. A method for identifying an interacting set of proteins comprising:
   A) generating first and second fragments of a fluorescent protein reporter molecule which have a directly fluorescent detectable activity when reconstituted and/or associated, wherein said fluorescent protein is selected from the group consisting of green fluorescent protein and mutants of green fluorescent protein;
   B) coupling said first fragments of said green fluorescent protein or mutant green fluorescent protein reporter molecule to members of a first panel of proteins;
   C) coupling said second fragments of said green fluorescent protein or mutant green fluorescent protein reporter molecule to members of a second panel of proteins;
   D) mixing the products of B) and C);
   E) directly testing for fluorescence of said green fluorescent protein or mutant green fluorescent protein reporter molecule when reconstituted and/or associated; and
   F) identifying the protein panel members whose interaction resulted in fluorescence of said green fluorescent protein or mutant green fluorescent protein reporter molecule and which thus form an interacting set.

2. A method for identifying an interacting set of proteins comprising:
   A) identifying a first panel and a second panel of proteins whose mutual interaction is desired to be tested;
   B) coupling proteins of said first panel to first fragments of a green fluorescent protein or mutant green fluorescent protein reporter molecule;
   C) coupling proteins of said second panel to second fragments of said green fluorescent protein or mutant green fluorescent protein reporter molecule; wherein said first and second fragments have no fluorescent activity prior to step (D)
   D) mixing the products of B) and C);
   E) directly testing for fluorescent activity of said green fluorescent protein or mutant green fluorescent protein reporter molecule; and
   F) identifying the protein panel members whose interaction resulted in said fluorescent activity and which thus form an interacting set.

3. A method of screening multiple panels of proteins against each other to determine the ability of individual protein panel members to interact with each other, said method comprising:
   A) coupling first fragments and second fragments of a green fluorescent protein or mutant green fluorescent protein reporter molecule to different protein panel members; wherein said first and second fragments have no detectable activity;

B) mixing the products of A);

C) testing for said green fluorescent protein or mutant green fluorescent protein reporter molecule activity; and D) identifying the protein panel members whose interaction results in said fluorescent protein reporter molecule activity and which thus form interacting members.

4. A method according to any one of claims 1-3 where at least two of said panels comprise a library of proteins.

5. A method according to any one of claims 1-3 where at least one of said panels comprise a library of proteins.

6. A method of preparing an assay system comprising:

A) identifying a first panel of proteins and a second panel of proteins whose mutual interaction is desired to be tested;

B) coupling molecules of said first panel of proteins to first fragments of a green fluorescent protein or mutant green fluorescent protein reporter molecule; and C) coupling molecules of said second panel of proteins to second fragments of said green fluorescent protein or mutant green fluorescent protein reporter molecule wherein said first and second fragments have no detectable fluorescent activity.

7. A method for identifying interacting proteins comprising:

(A) generating fragments of a green fluorescent protein or mutant green fluorescent protein reporter molecule, said fragments having a directly detectable activity when associated;

(B) coupling first fragments of said green fluorescent protein or mutant green fluorescent protein reporter molecule to members of a panel of proteins;

(C) coupling a second fragment of said green fluorescent protein or mutant green fluorescent protein reporter molecule to a second protein;

(D) mixing the products of B) and C);

(E) directly testing for said green fluorescent protein or mutant green fluorescent protein reporter molecule activity; and (F) identifying the panel of protein members whose interaction with said second protein resulted in said fluorescent protein reporter molecule activity.

8. A method for identifying interacting proteins comprising:

(A) identifying a panel of proteins and identifying a second protein whose interaction with members of said panel is desired to be tested;

(B) coupling members of said panel of proteins to first fragments of a green fluorescent protein or mutant green fluorescent protein reporter molecule;

(C) coupling the second protein to a second fragment of said green fluorescent protein or mutant green fluorescent protein reporter molecule wherein said first and second fragments have no detectable fluorescent activity;

(D) mixing the products of B) and C);

(E) directly testing for said green fluorescent protein or mutant green fluorescent protein reporter molecule activity; and (F) identifying the panel of protein members whose interaction with said second protein resulted in said fluorescent protein reporter molecule activity and which thus form interacting proteins.

9. A method of screening a first protein against a panel of proteins to determine the ability of said first protein to interact with individual members of said panel of proteins comprising:

A) coupling a first fragment of a green fluorescent protein or mutant green fluorescent protein reporter molecule to said first protein;

B) coupling second fragments of said green fluorescent protein or mutant green fluorescent protein reporter molecule to different members of said panel of proteins wherein said first and second fragments have no detectable fluorescent activity;

C) mixing the products of A) and B);

D) testing for fluorescent activity of said green fluorescent protein or mutant green fluorescent protein reporter molecule; and E) identifying the members of said panel of proteins whose interaction with said first protein results in said fluorescent protein reporter molecule fluorescent activity and which thus interact with said first protein.

10. A method according to any one of claims 7-9 wherein said panel comprises a library of proteins.

11. A method of preparing an assay system comprising: (A) identifying a panel of proteins whose interactions with a second protein are desired to be tested; (B) coupling members of said panel of proteins to first fragments of a green fluorescent protein or mutant green fluorescent protein reporter molecule; and (C) coupling said second protein to a second fragment of said green fluorescent protein or mutant green fluorescent protein reporter molecule wherein said first and second fragments have no detectable fluorescent activity.

12. A method for identifying interacting proteins comprising: (A) generating fragments of a green fluorescent protein or mutant green fluorescent protein reporter molecule which have a directly fluorescent detectable activity when associated; (B) coupling a first fragment of said green fluorescent protein or mutant green fluorescent protein reporter molecule to a first protein; (C) coupling a second fragment of said green fluorescent protein or mutant green fluorescent protein reporter molecule to a second protein; (D) mixing the products of B) and C); and (E) directly testing for fluorescent activity of said fluorescent protein reporter molecule in the absence or presence of one or more chemical or biological compounds.

13. A method for identifying interacting proteins comprising:

A) identifying a first protein and a second protein whose interaction is desired to be tested;

B) coupling said first protein to a first fragment of a green fluorescent protein or mutant green fluorescent protein reporter molecule;

C) coupling said second protein to a second fragment of said green fluorescent protein or mutant green fluorescent protein reporter molecule wherein said first and second fragments have no detectable fluorescent activity;

D) mixing the products of B) and C);

E) directly testing for fluorescent activity of said fluorescent protein reporter molecule.

14. A method of preparing an assay system comprising:

A) identifying a first protein and a second protein whose interaction is desired to be tested;

B) coupling said first protein to a first fragment of a green fluorescent protein or mutant green fluorescent protein reporter molecule; and C) coupling said second protein to a second fragment of said green fluorescent protein or mutant green fluorescent protein reporter molecule wherein said first and second fragments have no detectable fluorescent activity.

15. A method according to any one of claims 1-3, 6, 7-9, 11, 12-13, and 14 wherein said green fluorescent protein reporter molecule generates an optically detectable signal.

16. A method according to any one of claims 1-3, 6, 7-9, 11, 12-13, and 14 wherein said reporter molecule generates a fluorescent signal.

17. A method according to any one of claims 1-3, 6, 7-9, 11, 12-13, and 14 wherein said fluorescent protein reporter molecule generates a signal that can be quantified within living cells.

18. A method according to any one of claims 1-3, 6, 7-9, 11, 12-13, and 14 wherein said fluorescent protein reporter molecule generates a signal that can be localized within living cells.

19. A method according to any one of claims 1-3, 6, 7-9, 11, 12-13, and 14 wherein the fluorescent protein reporter molecule activity is detected by one or more methods selected from the group consisting of: cell color, fluorescence, optical density, spectroscopy, flow cytometry, microscopy, or image analysis.

* * * * *